US011091446B2

(12) United States Patent
Dube et al.

(10) Patent No.: US 11,091,446 B2
(45) Date of Patent: Aug. 17, 2021

(54) METHODS OF SELECTIVELY FORMING SUBSTITUTED PYRAZINES

(71) Applicant: R. J. Reynolds Tobacco Company, Winston-Salem, NC (US)

(72) Inventors: Michael Francis Dube, Winston-Salem, NC (US); William Monroe Coleman, III, Winston-Salem, NC (US)

(73) Assignee: R.J. Reynolds Tobacco Company, Winston-Salem, NC (US)

( * ) Notice: Subject to any disclaimer, the term of this patent is extended or adjusted under 35 U.S.C. 154(b) by 1058 days.

(21) Appl. No.: 15/468,665

(22) Filed: Mar. 24, 2017

(65) Prior Publication Data

US 2018/0273492 A1    Sep. 27, 2018

(51) Int. Cl.
| | | |
|---|---|---|
| *A24D 1/02* | (2006.01) | |
| *C07D 241/12* | (2006.01) | |
| *C07C 49/17* | (2006.01) | |
| *C07H 3/02* | (2006.01) | |
| *A24B 13/00* | (2006.01) | |
| *A24B 15/38* | (2006.01) | |

(52) U.S. Cl.
CPC ............ *C07D 241/12* (2013.01); *A24B 13/00* (2013.01); *A24B 15/38* (2013.01); *A24D 1/02* (2013.01)

(58) Field of Classification Search
CPC ...... C07D 242/12; C07C 49/17; A24D 1/002; A24D 1/02; A24F 47/002; C07H 3/02
See application file for complete search history.

(56) References Cited

U.S. PATENT DOCUMENTS

| | | | |
|---|---|---|---|
| 1,358,302 | A | 11/1920 | Ellis |
| 1,376,586 | A | 5/1921 | Schwartz |
| 1,915,428 | A | 6/1933 | Lambert |
| 2,766,148 | A | 10/1956 | Rowland |
| 2,774,680 | A | 12/1956 | Hackney et al. |
| 3,424,171 | A | 1/1969 | Rooker |
| 3,616,221 | A | 10/1971 | Takasaki |
| 3,696,917 | A | 10/1972 | Levi |
| 4,008,210 | A | 2/1977 | Steele et al. |
| 4,009,290 | A | 2/1977 | Okumori et al. |
| 4,045,879 | A | 9/1977 | Witte |
| 4,056,442 | A | 11/1977 | Huang et al. |
| 4,069,828 | A | 1/1978 | Hall et al. |
| 4,122,104 | A | 10/1978 | Witte |
| 4,131,118 | A | 12/1978 | Gellatly et al. |
| 4,144,895 | A | 3/1979 | Fiore |
| 4,150,677 | A | 4/1979 | Osborne, Jr. et al. |
| 4,244,381 | A | 1/1981 | Lendvay |
| 4,251,671 | A | 2/1981 | Alter et al. |
| 4,253,929 | A | 3/1981 | Keritsis |
| 4,267,847 | A | 5/1981 | Reid |
| 4,268,632 | A | 5/1981 | Wildman et al. |
| 4,289,147 | A | 9/1981 | Wildman et al. |
| 4,298,013 | A | 11/1981 | Semp et al. |
| 4,298,540 | A | 11/1981 | Youn et al. |
| 4,308,877 | A | 1/1982 | Mattina |
| 4,322,569 | A | 3/1982 | Chao et al. |
| 4,334,095 | A | 6/1982 | Baniel |
| 4,340,676 | A | 7/1982 | Bourque |
| 4,347,324 | A | 8/1982 | Wildman et al. |
| 4,351,346 | A | 9/1982 | Brummer et al. |
| 4,359,059 | A | 11/1982 | Brummer et al. |
| 4,359,417 | A | 11/1982 | Karnofsky et al. |
| 4,381,407 | A | 4/1983 | Bremus et al. |
| 4,400,471 | A | 8/1983 | Johal |
| 4,456,556 | A | 6/1984 | Grimsby |
| 4,456,557 | A | 6/1984 | Grimsby |
| 4,466,923 | A | 8/1984 | Friedrich |
| 4,476,881 | A | 10/1984 | Gravely et al. |
| 4,506,682 | A | 3/1985 | Muller |
| 4,513,756 | A | 4/1985 | Pittman et al. |
| 4,515,726 | A | 5/1985 | Sullivan |
| 4,528,993 | A | 7/1985 | Sensabaugh, Jr. et al. |
| 4,588,691 | A | 5/1986 | Johal |
| 4,589,428 | A | 5/1986 | Keritsis |
| 4,605,016 | A | 8/1986 | Soga et al. |
| 4,607,479 | A | 8/1986 | Linden |
| 4,612,942 | A | 9/1986 | Dobberstein et al. |

(Continued)

FOREIGN PATENT DOCUMENTS

| | | |
|---|---|---|
| CN | 1133694 | 10/1996 |
| CN | 1324586 | 12/2001 |

(Continued)

OTHER PUBLICATIONS

M. Climent et al., 5 ChemCatChem, 3866-3874 (2013) (Year: 2013).*
P. Vanessa et al., 58 Journal of Agricultural and Food Chemistry, 12523-12529 (2010) (Year: 2010).*
"Effect of Treatment of Tobacco with Ammonia or Various Ammonium Salts on the Levels of Pyridines and Pyrazines in Smoke," Truth Tobaco Industry Documents, University of California San Francisco, www.industrydocumentslibrary.ucsf.edu/tobacco/docs/lhvd0152, Published Dec. 10, 2010.

(Continued)

*Primary Examiner* — Brenda L Coleman
(74) *Attorney, Agent, or Firm* — Womble Bond Dickinson (US) LLP

(57) ABSTRACT

Methods of selectively forming substituted pyrazines are provided. Methods of the present invention can include receiving a reaction solution including at least one carbon source and at least one nitrogen source, and heating the reaction solution to a reaction temperature and holding the reaction solution at the reaction temperature for a time sufficient to produce a reaction product comprising at least one substituted pyrazine. The carbon source can be selected from the group consisting of hydroxy ketone(s), sugar(s) treated with at least one buffer, and combinations thereof. Tobacco products incorporating substituted pyrazines are also provided.

25 Claims, 8 Drawing Sheets

(56) References Cited

U.S. PATENT DOCUMENTS

| | | | |
|---|---|---|---|
| 4,622,982 A | 11/1986 | Gaisch et al. |
| 4,624,269 A | 11/1986 | Story et al. |
| 4,631,899 A | 12/1986 | Nielsen |
| 4,716,911 A | 1/1988 | Poulose et al. |
| 4,727,889 A | 3/1988 | Niven, Jr. et al. |
| 4,847,106 A | 7/1989 | Pike et al. |
| 4,887,618 A | 12/1989 | Bernasek et al. |
| 4,895,175 A | 1/1990 | Baskevitch et al. |
| 4,941,484 A | 7/1990 | Clapp et al. |
| 4,967,771 A | 11/1990 | Fagg et al. |
| 4,967,773 A | 11/1990 | Shaw |
| 4,986,286 A | 1/1991 | Roberts et al. |
| 4,987,907 A | 1/1991 | Townend |
| 4,991,599 A | 2/1991 | Tibbetts |
| 5,005,593 A | 4/1991 | Fagg |
| 5,018,540 A | 5/1991 | Grubbs et al. |
| 5,060,669 A | 10/1991 | White et al. |
| 5,065,775 A | 11/1991 | Fagg |
| 5,074,319 A | 12/1991 | White et al. |
| 5,077,071 A | 12/1991 | Strop |
| 5,092,352 A | 3/1992 | Sprinkle, III et al. |
| 5,099,862 A | 3/1992 | White et al. |
| 5,110,605 A | 5/1992 | Acharya |
| 5,121,757 A | 6/1992 | White et al. |
| 5,131,415 A | 7/1992 | Munoz et al. |
| 5,143,097 A | 9/1992 | Sohn et al. |
| 5,148,819 A | 9/1992 | Fagg |
| 5,159,942 A | 11/1992 | Brinkley et al. |
| 5,167,244 A | 12/1992 | Kjerstad |
| 5,197,494 A | 3/1993 | Kramer |
| 5,230,354 A | 7/1993 | Smith et al. |
| 5,234,008 A | 8/1993 | Fagg |
| 5,235,992 A | 8/1993 | Sensabaugh, Jr. |
| 5,243,999 A | 9/1993 | Smith |
| 5,258,194 A | 11/1993 | Anderson et al. |
| 5,296,621 A | 3/1994 | Roos et al. |
| 5,301,694 A | 4/1994 | Raymond et al. |
| 5,304,648 A * | 4/1994 | Chen .............. C07D 405/06 544/405 |
| 5,318,050 A | 6/1994 | Gonzalez-Parra et al. |
| 5,343,879 A | 9/1994 | Teague |
| 5,346,734 A | 9/1994 | Wydick, Jr. |
| 5,360,022 A | 11/1994 | Newton et al. |
| 5,387,416 A | 2/1995 | White et al. |
| 5,397,571 A | 3/1995 | Roland et al. |
| 5,426,220 A | 6/1995 | Baniel et al. |
| 5,435,325 A | 7/1995 | Clapp et al. |
| 5,445,169 A | 8/1995 | Brinkley et al. |
| 5,533,530 A | 7/1996 | Young et al. |
| 5,715,844 A | 2/1998 | Young et al. |
| 5,724,998 A | 3/1998 | Gellatly et al. |
| 5,733,574 A | 3/1998 | Dam |
| 5,859,263 A | 1/1999 | Ghorpade et al. |
| 5,932,095 A | 8/1999 | Walters et al. |
| 6,033,895 A | 3/2000 | Garger et al. |
| 6,083,729 A | 7/2000 | Martin et al. |
| 6,131,584 A | 10/2000 | Lauterbach |
| 6,162,516 A | 12/2000 | Derr |
| 6,216,706 B1 | 4/2001 | Kumar et al. |
| 6,225,471 B1 * | 5/2001 | Chen .............. C07D 241/12 544/410 |
| 6,225,483 B1 | 5/2001 | Franke |
| 6,248,760 B1 | 6/2001 | Wilhelmsen |
| 6,262,284 B1 | 7/2001 | Khachik |
| 6,280,761 B1 | 8/2001 | Santus |
| 6,298,858 B1 | 10/2001 | Coleman, III et al. |
| 6,298,859 B1 | 10/2001 | Kierulff et al. |
| 6,325,860 B1 | 12/2001 | Coleman, III |
| 6,403,126 B1 | 6/2002 | Webster et al. |
| 6,414,172 B1 | 7/2002 | Garcés et al. |
| 6,417,157 B1 | 7/2002 | Wadsworth et al. |
| 6,428,624 B1 | 8/2002 | Coleman, III et al. |
| 6,440,223 B1 | 8/2002 | Dube et al. |
| 6,495,175 B2 | 12/2002 | Rao et al. |
| 6,499,489 B1 | 12/2002 | Coleman, III |
| 6,504,085 B1 | 1/2003 | Howard |
| 6,591,841 B1 | 7/2003 | White et al. |
| 6,668,839 B2 | 12/2003 | Williams |
| 6,676,959 B1 | 1/2004 | Andersson et al. |
| 6,695,924 B1 | 2/2004 | Dube et al. |
| 6,772,767 B2 | 8/2004 | Mua et al. |
| 6,800,318 B2 | 10/2004 | Kapila et al. |
| 6,834,654 B2 | 12/2004 | Williams |
| 6,860,998 B1 | 3/2005 | Wilde |
| 6,895,974 B2 | 5/2005 | Peele |
| 6,953,040 B2 | 10/2005 | Atchley et al. |
| 7,025,066 B2 | 4/2006 | Lawson et al. |
| 7,032,601 B2 | 4/2006 | Atchley et al. |
| 7,067,718 B2 | 6/2006 | Anai et al. |
| 7,074,449 B1 | 7/2006 | Holley et al. |
| 7,156,981 B2 | 1/2007 | Wilde et al. |
| 7,179,930 B2 | 2/2007 | Bhaskaran et al. |
| 7,198,808 B2 | 4/2007 | Krasutsky et al. |
| 7,271,298 B2 | 9/2007 | Xu et al. |
| 7,337,782 B2 | 3/2008 | Thompson |
| 7,351,424 B2 | 4/2008 | Ornelas-Cravioto et al. |
| 7,374,779 B2 | 5/2008 | Chen et al. |
| 7,615,657 B2 | 11/2009 | Bathurst et al. |
| 7,622,599 B2 | 11/2009 | Swaminathan et al. |
| 7,629,007 B2 | 12/2009 | Peña |
| 7,638,314 B2 | 12/2009 | Zappi et al. |
| 7,652,167 B2 | 1/2010 | Miller et al. |
| 7,667,068 B2 | 2/2010 | Miller et al. |
| 7,671,242 B2 | 3/2010 | Losso et al. |
| 7,694,686 B2 | 4/2010 | Atchley et al. |
| 7,726,320 B2 | 6/2010 | Robinson et al. |
| 7,741,500 B2 | 6/2010 | Arhancet et al. |
| 7,810,507 B2 | 10/2010 | Dube et al. |
| 7,820,419 B2 | 10/2010 | Smith et al. |
| 7,861,728 B2 | 1/2011 | Holton, Jr. et al. |
| 7,901,512 B2 | 3/2011 | Quinter et al. |
| 7,910,209 B2 | 3/2011 | Uchida et al. |
| 7,943,350 B2 | 5/2011 | Vlasenko et al. |
| 8,061,362 B2 | 11/2011 | Mua et al. |
| 8,236,929 B2 | 8/2012 | Cheryan et al. |
| 8,247,423 B2 | 8/2012 | Estok et al. |
| 8,360,072 B2 | 1/2013 | Krauss |
| 8,389,749 B2 | 3/2013 | Dumesic et al. |
| 8,434,496 B2 | 5/2013 | Chen et al. |
| 8,695,609 B2 | 4/2014 | Dube et al. |
| 8,758,561 B2 | 6/2014 | Dittrich et al. |
| 8,807,141 B2 | 8/2014 | Breslin et al. |
| 8,893,725 B2 | 11/2014 | Dube et al. |
| 8,944,072 B2 | 2/2015 | Chen et al. |
| 8,955,523 B2 | 2/2015 | Coleman, III et al. |
| 8,991,403 B2 | 3/2015 | Chen et al. |
| 9,010,339 B2 | 4/2015 | Dube et al. |
| 9,254,001 B2 | 2/2016 | Hege Byrd et al. |
| 9,265,284 B2 | 2/2016 | Junker et al. |
| 9,402,415 B2 | 8/2016 | Coleman, III et al. |
| 2001/0016593 A1 | 8/2001 | Wilhelmsen |
| 2002/0197688 A1 | 12/2002 | Pandolfino |
| 2004/0020503 A1 | 2/2004 | Williams |
| 2004/0101543 A1 | 5/2004 | Liu et al. |
| 2004/0118422 A1 | 6/2004 | Lundin et al. |
| 2004/0173228 A1 | 9/2004 | Coleman, III |
| 2005/0061339 A1 | 3/2005 | Hansson et al. |
| 2005/0066986 A1 | 3/2005 | Nestor et al. |
| 2005/0115580 A1 | 6/2005 | Quinter et al. |
| 2005/0143464 A1 | 6/2005 | Matsuyama et al. |
| 2005/0147722 A1 | 7/2005 | Fan et al. |
| 2005/0244521 A1 | 11/2005 | Strickland et al. |
| 2006/0003036 A1 | 1/2006 | Shaath et al. |
| 2006/0120974 A1 | 6/2006 | Mcneight |
| 2006/0191548 A1 | 8/2006 | Strickland et al. |
| 2006/0198873 A1 | 9/2006 | Chan et al. |
| 2007/0007069 A1 | 1/2007 | Hamasaki et al. |
| 2007/0062549 A1 | 3/2007 | Holton, Jr. et al. |
| 2007/0105112 A1 | 5/2007 | Hitchman et al. |
| 2007/0137663 A1 | 6/2007 | Taylor et al. |
| 2007/0186942 A1 | 8/2007 | Strickland et al. |
| 2007/0193596 A1 | 8/2007 | Mori et al. |
| 2007/0277432 A1 | 12/2007 | Jackam et al. |
| 2008/0020050 A1 | 1/2008 | Chau et al. |

(56) References Cited

U.S. PATENT DOCUMENTS

| | | |
|---|---|---|
| 2008/0029110 A1 | 2/2008 | Dube et al. |
| 2008/0029116 A1 | 2/2008 | Robinson et al. |
| 2008/0029117 A1 | 2/2008 | Mua et al. |
| 2008/0173317 A1 | 7/2008 | Robinson et al. |
| 2008/0196730 A1 | 8/2008 | Engstrom et al. |
| 2008/0209586 A1 | 8/2008 | Nielsen et al. |
| 2008/0305216 A1 | 12/2008 | Crawford et al. |
| 2009/0025738 A1 | 1/2009 | Mua et al. |
| 2009/0025739 A1 | 1/2009 | Brinkley et al. |
| 2009/0028803 A1 | 1/2009 | Mishra et al. |
| 2009/0065013 A1 | 3/2009 | Essen et al. |
| 2009/0081291 A1 | 3/2009 | Gin et al. |
| 2009/0234146 A1 | 9/2009 | Cooney et al. |
| 2009/0293889 A1 | 12/2009 | Kumar et al. |
| 2009/0293895 A1 | 12/2009 | Axelsson et al. |
| 2010/0004294 A1 | 1/2010 | Axelsson et al. |
| 2010/0017916 A1 | 1/2010 | Pappan et al. |
| 2010/0018540 A1 | 1/2010 | Doolittle et al. |
| 2010/0018541 A1 | 1/2010 | Gerardi et al. |
| 2010/0037903 A1 | 2/2010 | Coleman, III et al. |
| 2010/0058655 A1 | 3/2010 | Fogher |
| 2010/0196980 A1 | 8/2010 | Smith et al. |
| 2010/0197029 A1 | 8/2010 | O'Fallon et al. |
| 2010/0239726 A1 | 9/2010 | Pertsovich |
| 2010/0282267 A1 | 11/2010 | Atchley |
| 2010/0286420 A1 | 11/2010 | Akatsuka et al. |
| 2010/0291245 A1 | 11/2010 | Gao et al. |
| 2011/0083683 A1 | 4/2011 | Krauss |
| 2011/0139164 A1 | 6/2011 | Mua et al. |
| 2011/0174323 A1 | 7/2011 | Coleman, III et al. |
| 2011/0247640 A1 | 10/2011 | Beeson et al. |
| 2011/0259353 A1 | 10/2011 | Coleman, III et al. |
| 2011/0315154 A1 | 12/2011 | Mua et al. |
| 2012/0037175 A1 | 2/2012 | Cantrell et al. |
| 2012/0040408 A1 | 2/2012 | Decker et al. |
| 2012/0055494 A1 | 3/2012 | Hunt et al. |
| 2012/0103353 A1 | 5/2012 | Sebastian et al. |
| 2012/0125354 A1 | 5/2012 | Byrd et al. |
| 2012/0138073 A1 | 6/2012 | Cantrell et al. |
| 2012/0138074 A1 | 6/2012 | Cantrell et al. |
| 2012/0141648 A1 | 6/2012 | Morton et al. |
| 2012/0152265 A1 | 6/2012 | Dube et al. |
| 2012/0192880 A1 | 8/2012 | Dube et al. |
| 2012/0192882 A1 | 8/2012 | Dube et al. |
| 2012/0211016 A1 | 8/2012 | Byrd, Jr. |
| 2012/0260929 A1 | 10/2012 | Coleman et al. |
| 2012/0272976 A1 | 11/2012 | Byrd et al. |
| 2012/0312314 A1 | 12/2012 | Plakidis et al. |
| 2013/0008457 A1 | 1/2013 | Zheng et al. |
| 2013/0014771 A1 | 1/2013 | Coleman, III et al. |
| 2013/0125907 A1 | 5/2013 | Dube et al. |
| 2013/0213417 A1 | 8/2013 | Chong et al. |
| 2013/0255702 A1 | 10/2013 | Griffith, Jr. et al. |
| 2013/0276801 A1 | 10/2013 | Byrd, Jr. et al. |
| 2013/0337431 A1 | 12/2013 | Anuradha |
| 2014/0000638 A1 | 1/2014 | Sebastian et al. |
| 2014/0020694 A1 | 1/2014 | Moldoveanu et al. |
| 2014/0060554 A1 | 3/2014 | Collett et al. |
| 2014/0096780 A1 | 4/2014 | Gerardi |
| 2014/0096781 A1 | 4/2014 | Sears et al. |
| 2014/0096782 A1 | 4/2014 | Ampolini et al. |
| 2014/0190497 A1 | 7/2014 | Dube et al. |
| 2014/0256829 A1 | 9/2014 | Junker |
| 2014/0271951 A1 | 9/2014 | Mua et al. |
| 2014/0271952 A1 | 9/2014 | Mua et al. |
| 2014/0273118 A1 | 9/2014 | Held et al. |
| 2015/0040922 A1 | 2/2015 | Dube et al. |
| 2015/0059780 A1 | 3/2015 | Davis et al. |
| 2015/0122271 A1 | 5/2015 | Chen et al. |
| 2015/0201669 A1 | 7/2015 | Junker et al. |
| 2016/0201102 A1 | 7/2016 | Zhu et al. |
| 2016/0257982 A1 | 9/2016 | Del Rio et al. |
| 2016/0376246 A1 | 12/2016 | Delcroix et al. |
| 2017/0215472 A1 | 8/2017 | Dube et al. |

FOREIGN PATENT DOCUMENTS

| | | |
|---|---|---|
| CN | 101262786 | 9/2008 |
| CN | 101450897 | 6/2009 |
| CN | 101801188 | 8/2010 |
| CN | 102079704 | 6/2011 |
| CN | 10218366 | 9/2011 |
| CN | 104 138 029 | 11/2014 |
| EP | 0 244 208 | 11/1987 |
| EP | 0 505 891 | 9/1992 |
| GB | 996141 | 6/1965 |
| GB | 1 202 821 | 8/1970 |
| GB | 2 020 538 A | 11/1979 |
| JP | 59-28465 A | 2/1984 |
| JP | H08-266260 | 10/1996 |
| JP | 1162008 | 10/1997 |
| JP | H11-308987 | 11/1999 |
| JP | H11-332408 | 12/1999 |
| JP | 2003024096 | 1/2003 |
| JP | 2009527488 | 7/2009 |
| KR | 930003904 | 5/1993 |
| KR | 10-2006-0054728 | 5/2006 |
| KR | 1020120022238 | 3/2012 |
| KR | 101233116 | 2/2013 |
| WO | WO 99/03842 | 1/1999 |
| WO | WO 02/083191 | 10/2002 |
| WO | WO 2004/095959 | 11/2004 |
| WO | WO 2005/004480 | 1/2005 |
| WO | WO 2005/016036 | 2/2005 |
| WO | WO 2005/027892 | 3/2005 |
| WO | WO 2005/041699 | 5/2005 |
| WO | WO 2005/063060 | 7/2005 |
| WO | WO 2007/104573 | 9/2007 |
| WO | WO 2008/092207 | 8/2008 |
| WO | WO 2009/015142 | 1/2009 |
| WO | WO 2009/075762 | 6/2009 |
| WO | WO 2009/110775 A1 | 9/2009 |
| WO | WO 2010/054198 A2 | 5/2010 |
| WO | WO 2010/093229 | 8/2010 |
| WO | WO 2010/132444 | 11/2010 |
| WO | WO 2013/158957 | 10/2013 |
| WO | WO 2015/052282 | 4/2015 |

OTHER PUBLICATIONS

"Enzyme Class Index: Hydrolases on esters", *Sigma-Aldrich*, 2014, [online], Retrieved from the Internet, [retrieved Oct. 21, 2014], URL:http://www.sigmaaldrich.com/life-science/metabolomics/enzyme-explorer/class-index/hydrolases-on-esters.html.

"Recrystallization," University of Toronto, https://web.archive.org/web/201410291407330/http://www.chem.utoronto.ca/coursenotes/CHM249/Recrystallization.pdf, Published: Oct. 29, 2014.

Akpinar et al., "Enzymatic Production of Xylooligosaccharide from Selected Agricultural Wastes," *Food and Bioproducts Processing*, 2009, pp. 145-151, vol. 87.

Alonso et al., "Integrated Conversion of Hemicellulose and Cellulose from Lignocellulosic Biomass," *Energy & Environmental Science*, 2013, vol. 6, pp. 76-80.

Alpert, H.R., et al., "A study of pyrazines in cigarettes and how additives might be used to enhance tobacco addiction," *Tobacco Control*, Jun. 2015, vol. 25(4), pp. 444-450.

Anonymous, "Cellulosic Sugars—Wikipedia", Nov. 29, 2016, XP055363042, Retrieved from the internet: URL: https://enwikipedia.org/wiki/Cellulosic_sugars [retrieved on Apr. 7, 2017].

Brandes, S., "Ueber pyrazine and piperazine," *Journal Fuer Praktische Chemie*, 1896, vol. 2(54), pp. 481-495.

Brandt et al., "Practical Aspects of Preparative HPLC in Pharmaceutical and Development Production", *LC·GC Europe*, Mar. 2002, pp. 2-5.

Bryzgalov et al., "Comparative Life Cycle Assessment of General Loose and Portion Snus", *IN1800 Life Cycle Assessment*, May 26, 2005, pp. 3-23.

Chu et al., "Fatty Acid Composition in Tobacco, I. Green Tobacco Plants", *Plant Physiology*, American Society of Plant Biologists,

(56) References Cited

OTHER PUBLICATIONS

Mar. 1968, pp. 428-433, vol. 43(3), [online], retrieved from the internet, [retrieved Jun. 24, 2015], URL:http://www.ncbi.nlm.nih.gov/pmc/articles/PMC1086856/.
Clark et al., "Derivatization Solid-Phase Microextraction Gas Chromatographic-Mass Spectrometric Determination of Organic Acids in Tobacco"; 1997; Journal of Chromatographic Science; vol. 35; pp. 209-212.
Coleman III, "On the synthesis and characteristics of aqueous formulations rich in pyrazines, in Flavor Fragrance and Odor Analysis," Second Edition, Ray Marsili, ed., Chapter 7, pp. 135-182, CRC Press, Boca Raton, 2012.
Coleman, III et al., "Sugar and selected amino acid influences on the structure of pyrazines in microwave heat-treated formulations," *J. Sci. Food Agric.*, 2006, vol. 86, pp. 380-391.
Coleman, III et al., "Headspace Solid-Phase Microextraction Analysis of Artificial Flavors", *J. Sci. Food Agric.*, 2005, pp. 2645-2654, vol. 85.
Coleman, III et al., "The Use of a Non-Equilibrated Solid Phase Microextraction Method to Quantitatively Determine the Off-Notes in Mint and Other Essential Oils", *J. Sci. Food Agric.*, 2004, pp. 1223-1228, vol. 84.
Crabbe et al., "Biodiesel Production of Crude Palm Oil and Evaluation of Butanol Extraction and Fuel Properties," *Process Biochemistry*, 37, 65-71, (2001).
Dasari, M. A., "Catalytic conversion of glycerol and sugar alcohols to value-added products", Univ. Missouri-Columbia, ISBN-10, 0549727582, 2006, pp. 264.
Ejikeme et al., "Catalysis in Biodiesel Production by Trans-Esterification Processes: An Insight," *Journal Chemistry*, 7, 1120-1132 (2010).
Elmore, J.S., et al., "Effects of Sulphur nutrition during potato cultivation on the formation of acrylamide and aroma compounds during cooking," *Food Chemistry*, Oct. 2010, vol. 122(3), pp. 753-760.
Epino, R. M., "Paper from Tobacco Stalks," Philippine STAR, 2004, https_//www.philstar.com/business/agriculture/2004/02/29/240762/paper-tobacco-stalks.
Freedman et al., "Trans-Esterification Kinetics of Soybean Oil," *JAOCS*, 63, 1375-1380 (1986).
Frega et al., "Chemical composition of Tobacco Seeds (*Nicotiana tabacum* L.)," *JAOCS*, 1991, pp. 20-33, vol. 68(1).
Giannelos et al., "Tobacco Seed Oil as an Alternative Diesel Fuel: Physical and Chemical Properties", *Industrial Crops and Products*, 2002, vol. 16, pp. 1-9.
Hayami, J., "Studies on the Chemical Decomposition of Simple Sugars. XII. Mechanism of the Acetol Formation," *Bull. Chem. Soc. Japan*, 1961, vol. 34, pp. 927-932.
Ishikawa et al., "Water-Soluble Constituents of Dill", *Chem. Pharm. Bull.*, 2002, pp. 501-507, vol. 50, No. 4.
Kodama et al., "Isolation of a New Terpene Glucoside, 3-Hydroxy-5, 6-epoxy-β-ionyl-β-D-glucopyranoside from Flue-cured Tobacco", *Agric. Biol. Chem.*, 1981, pp. 941-944, vol. 45, No. 4.
Kolah et al. (2008), "Triethyl Citrate Synthesis by Reactive Distillation," *Industrial and Engineering Chemistry Research*, vol. 47, No. 4, pp. 1017-1024.
Kolah et al. "Reaction Kineticsof the Catalytic Esterification of Citric Acid with Ethanol", 2007; Industrial Engineering and Chemistry Research; vol. 46; pp. 3180-3187; American Chemical Society.
Lancker, F.V., et al., "Formation of Pyrazines in Maillard Model Systems of Lysine-Containing Dipeptides," *Journal of Agricultural and Food Chemistry*, Feb. 2010, vol. 58(4), pp. 2470-2478.
Leffingwell & Associates, Ester Detection Thresholds and Molecular Structures, www.leffingwell.com/esters, downloaded Sep. 23, 2015.
Leffingwell et al., "Tobacco Flavoring for Smoking Products", *R. J. Reynolds Tobacco Company*, 1972, pp. 1-72.
Li et al. Nanfang Nongye Xuebao. 2012. vol. 43, No. 8, pp. 1158-1163. CAPLUS Abstract enclosed.
Liu et al. J. Henan Agricult. Sci. 2012. vol. 41, No. 9, pp. 50-52. CAPLUS Abstract enclosed.
Loughrin et al.," Glycosidically Bound Volatile Components of *Nicotiana sylvestris* and *N. Suaveolens* Flowers", *Phytochemistry*, 1992, pp. 1537-1540, vol. 31, No. 5.
Loughrin et al., "Headspace Compounds from Flowers of *Nicotiana tabacum* and Related Species", *J. Agric. Food Chem.*, 1990, vol. 38, No. 2, pp. 455-460.
Marchetti, J.M., et al., "Possible Methods for Biodiesel Production," Renewable and Sustainable Energy Review, 2007, pp. 1300-1311, vol. 11(6).
Matsumura et al., "Water-Soluble Constituents of Caraway: Carron Derivatives and their Glucosides", *Chem. Pharm. Bull.*, 2002, pp. 66-72, vol. 50, No. 1.
Matsuzaki et al., "Novel Glycerolipids and Glycolipids from the Surface Lipids of Nicotiana Benthamiana," *Biosci. Biotech. Biochem.*, Mar. 1992, pp. 1565-1569, vol. 56(10).
Mohamad, M. H., et.al., "A review of acetol: application and production," *Amer. J. Appl. Sci.*, 2011, vol. 8, pp. 1135-1139.
Moldoveanu et al., "Dual Analysis of Triglycerides from Certain Common Lipids and Seed Extracts," *J. Agric.Food Chem.*, 59, 2137-2147 (2011).
Moldoveanu, "5. Profiling of lipids from fruit and seed extracts", Lipidomics: Sea Food, Marine Based Dietary Supplement, *Fruit and Seed*, 2012: pp. 73-123, Ed. Su Chen [online], Retrieved from the Internet, [retrievedOct. 21, 2014], URL:http://www.trures.com/ebook/uploads/suchencontent/T_13743193085%20Su%20Chen.pdf.
Mukhtar et al., "Fatty Acid Composition of Tobacco Seed Oil and Synthesis of Alkyd Resin", *Chin. J. of Chem.*, 2007, vol. 25, No. 5, pp. 705-708.
Nakka, R. "Purification of Low-Grade Potassium Nitrate," Richard Nakka's Experimental Rocketry Website, Apr. 3, 2008.
Novotny, et al., "Formation of alpha-hydroxycarbonyl and alpha-dicarbonyl compounds during degradation of monosaccharides," Czech J. Food Sci., 2007, vol. 25, pp. 119-130.
O'Deen, W. A., et al., "Devarda's Alloy Reduction of Nitrate and Tube Diffusion of the Reduced Nitrogen for Indophenol Ammonium and Nitrogen-15 Determinations," Analytical Chemistry, 1980, vol. 52, pp. 1164-1166.
Ochiai, N., "6 Times Faster Screening of Pesticide Multi-Residues in Aqueous Samples Take Two!" *Gerstel Solutions Worldwide*, 2006, pp. 17-19, No. 6.
Patel et al., "Production Potential and Quality Aspects of Tobacco Seed Oil", *Tob. Res.*, 1998, vol. 24, No. I, pp. 44-49.
Perflavoiy Information System, www.perflavory.com, downloaded Sep. 23, 2015.
Raguso et al., "Fragrance Chemistry, Nocturnal Rhythms and Pollination "Syndromes" in *Nicotiana"*, *Phytochemistry*, 2003, pp. 265-284, vol. 63.
Ralph et al., "NMR Characterization of Altered Lignins Extracted from Tobacco Plants Down-Regulated for Lignification Enzymes Cinnamyl-Alcohol Dehydrogenase and Cinnamoyl-CoA Reductase," *Proeccedings of the National Academy of Sciences*, 1998, vol. 95, pp. 12803-12808. http://www.ncbi.nlm.nih.gov/pmc/articles/PMC23601/.
Sadecka, et al.; Determination of organic acids in tobacco by capillary isotachophoresis; 2003; Journal of Chromatography A; vol. 988; pp. 161-165; Elsevier Science B.V.
Sahraoui et al., "Improved Microwave Steam Distillation Apparatus for Isolation of Essential Oils Comparison with Conventional Steam Distillation", *J. Chromatogr. A.*, 2008, pp. 229-233.
Satynaryana Murthy, "Performance of Tobacco Oil Based Bio-Diesel Fuel in a Single cylinder Direct Injection Engine,"*International J. Physical Sci.*, 5, 2066-2074 (2010).
Scalone, G.L.L., et al., "Influence of Free Amino Acids, Oligopeptides, and Polypeptides on the Formation of Pyrazines in Maillard Model Systems," *Journal of Agricultural and Food Chemistry*, Jun. 2015, vol. 63(22), pp. 5364-5372.
Schuchardt et al., "Trans-Esterification of Vegetable Oils: A Review," Chem. Soc., 9, 199-210 (1998).

(56) References Cited

OTHER PUBLICATIONS

Shaw, P. F., et al., "Base catalyzed fructose degradation and its relation to nonenzymic browning," *J. Agric. Food Chem.*, 1968, vol. 16(6), pp. 979-982.

Shibamoto, T., et al., "Effect of time, temperature, and reactant ration on pyrazine formation in model systems," *J. Agric. Food Chem.*, 24, (1976) p. 847.

Shmuk (1934), "The Method of Determination of Citric and Malic Acids in Tobacco and Makhorka" Ibid., pp. 247-251.

Shmuk et al. (1930), "Investigation of the Tobacco Acids," in Works of Academician A.A. Shmuk, vol. III, The Chemistry and Technology of Tobacco (Moscow: Pishchepromidzat, 1953; Jerusalem: trans. Lengy et al., Israel Program for Scientific Translations, 1961), pp. 136-144.

Shmuk et al. (1933), "Tobacco and Makhorka as Raw Materials for the Production of Citric Acid," in Works, op. cit., pp. 688-707.

Siti Solehah et al. "Effect of Temperature and pH on Glucose Production Using Enzymatic Hydrolysis," Apr. 1, 2010, XP055363092, Retrieved from the Internet: URL: http://umpir.ump_edu_my/3287/1/CD5873_SITI_SOLEHAH_AHMAD.pdf [Retrieved on Apr. 7, 2017].

Snook et al., "The Flower Flavonols of *Nicotiana* Species", *Phytochemistry*, 1992, pp. 1639-1647, vol. 31, No. 5.

Song, L., et al., "One-pot synthesis of 2-hydroxymethyl-5-methylpyrazine from renewable 1,3-dihydroxyacetone," *Green Chemistry*, May 2017, vol. 19(15), pp. 3515-3519.

Stanesh, *Biochemistry*, Chapter 6. Lipids and Membranes, Springer Science+Business Media, 1998, pp. 141-144.

Stanisavljevic et al., "Comparison of techniques for the Extraction of Tobacco Seed Oil", *Eur. J. Lipid Sci. Technol.*, 2009, vol. 111, pp. 513-518.

Stanisavljević et al., "Ultrasonic extraction of oil from tobacco (*Nicotiana tabacum* L.) seeds", *Ultrasonics Sonochemistry*, 2007, pp. 646-652, vol. 14, No. 5.

Tashpulatov, et al., "Enzymatic Production of Glucose Syrups from Cellulose-Containing Plant Wastes," *Chemistry of Natural Compounds*, vol. 33, No. 3, 1997.

Tienpont et al., "Stir Bar Sorptive Extraction-Thermal Desorption-Capillary GC-MS Applied to Biological Fluids", *Anal. Bioanal. Chem. . .* , 2002, pp. 46-55, vol. 373.

Tso (1972), Physiology and Biochemistry of Tobacco Plants (Stroudsburg: Dowden, Hutchinson and Ross), p. 205.

TurboVap® II brochure, Biotage, 2010, [online], retrieved from the Internet, [retrieved Dec. 1, 2015], URL:http://www.google.com/url?sa=t&ret=j&q=&esre=s&source=web&cd=11&ved=0ahUKEwiKyOzrh7yJAhULx2MKHOYRAILQFghKMAo&url=http%3A%2F%2Fwww.uniscience.combr%2Fcorantes-fluorescentes-de-membrana-biotium%2Fdioc5-3-3-3-dipentyloxacarbocyanine-iodide-bio...

Veljkovic, V. B., et al., "Biodiesel Production from Tobacco Seed Oil with a High Content of Free Fatty Acids," *Fuel*, 2006, pp. 2671-2675, vol. 85(17).

Vickery et al. The Non-Volatile Organic Acids of Green Tobacco Leaves; 1931; Journal of Biological Chemistry; vol. 90; pp. 637-653.

Weenen, H., et al., "Carbohydrate Cleavage in the Maillard Reaction", Flavor Science, Recent Developments, A. Taylor and D. Mottram, eds., Royal Society of Chemistry, Special Publication # 197, Cambridge, 1996.

Winayanuwattikun, P., et al., "Potential Plant Oil Feedstock for Lipase-Catalyzed Biodiesel Production in Thailand," Biomass and Bioenergy, 2008, pp. 1279-1286, vol. 32(12).

Wu et al. Yunnan Nongye Daxue Xuebao. 2013. vol. 28, No. 3, pp. 353-359. CAPLUS Abstract enclosed.

Xi et al. Yancao Keji. 2011. vol. 5, pp. 29-33. CAPLUS Abstract enclosed.

Yan, W., "Gas phase conversion of sugars to C3 chemicals," PhD Thesis, University of Missouri-Columbia, 2008.

Zhang et al., "Advances in the Catalytic Production and Utilization of Sorbitol," *Industrial & Engineering Chemistry Research*, 2013, vol. 52, p. 11799-11815.

Zhang, Yi-Heng Percival et al., "Toward an Aggregated Understanding of Enzymatic Hydrolysis of Cellulose: Noncomplexed Cellulase Systems," Wiley InterScience. Biotechnology and Bioengineering, vol. 88, No. 7, Dec. 30, 2004, p. 797-824.

Ziaie-Shirkolaee et al. "Study on Cellulose Degradation During Organosolv Delignification of Wheat Straw and Evaluation of Pulp Properties," *Iranian Polymer Journal*, 2007, pp. 83-96, vol. 16(2).

\* cited by examiner

METHODS OF SELECTIVELY FORMING SUBSTITUTED PYRAZINES

FIELD OF THE INVENTION

The present invention relates to methods of forming substituted pyrazines. Of particular interest are methods of selectively forming targeted substituted pyrazines.

BACKGROUND OF THE INVENTION

Pyrazines are produced by reactions (e.g., Maillard) of a carbon source with nitrogenous compounds, such as amino acids and bases (e.g., diammonium phosphate (DAP), NaOH). In many conventional reaction pathways intended to produce pyrazines, a sugar (e.g., fructose, glucose, fructose/glucose mixtures, rhamnose) is used as the carbon source. To date, the vast majority of model reactions and fortified natural products which result in pyrazine-rich formulations upon heating have used sugars such as fructose, glucose, fructose/glucose mixtures, and rhamnose as the carbon source components of the formulations. These sugars have been shown to serve as carbon sources for the formation of the pyrazine aromatic ring structure. See, e.g., U.S. Pat. App. Pub. Nos. 2004/0173228 to Coleman, 2010/0037903 to Coleman et al., 2012/0152265 to Dube et al., 2012/0260929 to Coleman et al., 2013/0125907 to Dube et al., 2013/0337418 to Anuradha, 2015/0040922 to Dube et al., and 2015/0122271 to Chen et al.; U.S. Pat. No. 5,258,194 to Anderson et al., U.S. Pat. No. 6,298,858 to Coleman; U.S. Pat. No. 6,325,860 to Coleman, U.S. Pat. No. 6,440,223 to Dube et al., U.S. Pat. No. 6,499,489 to Coleman; U.S. Pat. No. 6,591,841 to White et al., U.S. Pat. No. 6,695,924 to Dube et al., U.S. Pat. No. 8,434,496 to Chen et al., U.S. Pat. No. 8,944,072 to Brinkley et al., U.S. Pat. No. 8,955,523 to Coleman et al., U.S. Pat. No. 8,991,403 to Chen et al., U.S. Pat. No. 9,010,339 to Dube et al., U.S. Pat. No. 9,254,001 to Byrd et al., U.S. Pat. No. 9,265,284 to Junker et al., and U.S. Pat. No. 9,402,415 to Coleman et al.; and Coleman III, On the synthesis and characteristics of aqueous formulations rich in pyrazines, in Flavor Fragrance and Odor Analysis, Second Edition, Ray Marsili, ed., Chapter 7, pp 135-182, CRC Press, Boca Raton, 2012; each of which is herein incorporated by reference in its entirety.

Most often, these reactions with sugar(s) and a nitrogen source have employed ammonium hydroxide and/or free amino acids as nitrogen sources that furnish the nitrogen bond within the pyrazine structure. See, e.g., Effect of time, temperature, and reactant ratio on pyrazine formation in model system, T. Shibamoto, R. A. Bernhard, J. Agric. Food Chem., 24, (1976) p. 847. The reaction produces a complex mixture of many substituted pyrazines. When a sugar serves as the sole carbon source in the reaction to produce pyrazines, the molecules pyrazine and methylpyrazine are the dominant pyrazines produced, often much greater than 60% of the total pyrazine yield. Even when free amino acids are employed as co-reagents in an attempt to reduce the amount of pyrazine and methylpyrazine molecules produced, this trend is evident.

From a sensory perspective, the molecules pyrazine and methylpyrazine possess neither desirable sensory notes nor acceptable volatility characteristics for use in tobacco products. Thus, their presence in a mixture of pyrazines is a less than desirable characteristic for certain applications.

As such, it would be desirable to provide methods for selectively producing certain desirable substituted pyrazines in greater amounts.

SUMMARY OF THE INVENTION

The present invention provides methods of selectively forming certain substituted pyrazines. A method of selectively producing pyrazines can comprise receiving a reaction solution comprising at least one tobacco-derived carbon source (e.g., a hydroxy ketone and/or at least one sugar treated with a buffer) and at least one tobacco-derived nitrogen source (e.g., a protein and/or an amino acid), and heating the reaction solution to a reaction temperature and holding the reaction solution at the reaction temperature for a time sufficient to produce a reaction product comprising at least one substituted pyrazine. The nitrogen source can be selected from the group consisting of amino acids, ammonium ions, and combinations thereof.

In various embodiments, the at least one substituted pyrazine can be selected from the group consisting of 2,6-dimethylpyrazine; 2,5-dimethylpyrazine; 2-ethyl-5-methylpyrazine; 2-ethyl-6-methylpyrazine; 2,3,5-trimethylpyrazine; 2-ethyl-3,5-dimethylpyrazine; 2-ethyl-2,5-dimethylpyrazine; 2,3,5,6-trimethylpyrazine; 2,3,5-trimethyl-6-ethylpyrazine; 2,6-dimethyl-3-propylpyrazine; 2,5-diethyl-3,6-dimethylpyrazine; 2,6-dimethyl-3-(2-methylbutyl)pyrazine; 2,5-dimethyl-3-(2-methylbutyl)pyrazine; 2,5-dimethyl-3-(3-methylbutyl)pyrazine; 2,5-dimethyl-3-propylpyrazine; 2,5-dimethyl-3-cis-propenylpyrazine; 2-isopropenyl-3,6-dimethylpyrazine; 2-(2-methylpropyl)-3,5-dimethylpyrazine; 2,6-dimethyl-3-isobutylpyrazine; 2-(2-methylpropyl)-3,5,6-trimethylpyrazine, 2,3-dimethylpyrazine; trimethylpyrazine; furaneol, 2,5-dimethyl-3-ethylpyrazine; tetramethylpyrazine; 2,3-diethyl-5-methylpyrazine; 2,5-dimethyl-3-propenylpyrazine; 2,3,5-trimethyl-6-isopropylpyrazine; 2-acetyl-4,5-dimethylpyrazine; 3,5-dimethyl-2-methylpropylpyrazine; 2,6-diethylpyrazine; 2,5-diethylpyrazine; 2-ethyl-3,5,6-trimethylpyrazine; 3.5-dimethyl-2-(n-propyl)pyrazine; 3,6-dimethyl-2-(n-propyl)pyrazine; 2,5-diethyl-3-methylpyrazine; 2,3-diethyl-5,6-dimethylpryazine; trans-3-methyl-2-(n-propyl)-6-(butenyl)pyrazine; 2,5,7-trimethyl-6,7-dihydro-5H-cyclopentapyrazine; and 2,5-dimethyl-3-ethylpyrazine; and combinations thereof.

In some embodiments, the at least one substituted pyrazine is disubstituted, trisubstituted, or tetrasubstituted. In certain embodiments, the at least one substituted pyrazine comprises at least one substituent group having 2 or more carbon atoms. In various embodiments, the at least one substituted pyrazine comprises at least one substituent group having 3 or more carbon atoms.

In various embodiments, the method of selectively forming certain substituted pyrazines can further comprise isolating the at least one substituted pyrazine from the reaction product. The step of isolating the at least one tobacco-derived pyrazine from the reaction product can comprise at least one of liquid-liquid extraction of the reaction product, liquid-solid extraction of the reaction product, and simple distillation of the reaction product, for example.

The methods of the present invention can further comprise incorporating at least one substituted pyrazine into a tobacco product. In certain embodiments, the tobacco product can be a smoking article. In some embodiments, the tobacco product can be a smokeless tobacco product.

In various embodiments of the present invention, a method of forming pyrazines is provided, the method comprising receiving a reactant solution comprising at least one alpha-hydroxy ketone and at least one nitrogen source, and heating the reactant solution to a reactant temperature and holding the reactant solution at the reactant temperature for a time sufficient to produce a reactant product comprising at least one substituted pyrazine. Various embodiments of the method can further comprise isolating the at least one substituted pyrazine from the reactant product. In certain embodiments, the at least one hydroxy ketone can comprise acetol and the at least one substituted pyrazine can be selected from the group consisting of: 2,3-dimethylpyrazine; 2,6-dimethylpyrazine; 2-ethyl-6-methylpyrazine; 2-ethyl-5-methylpyrazine; trimethylpyrazine; furaneol; 2,5-dimethyl-3-ethylpyrazine; 2-ethyl-3,5-dimethylypyrazine; tetramethylpyrazine; 2,5-dimethyl-3-propenylpyrazine; 2,3,5-trimethyl-6-isopropylpyrazine; 2-acetyl-4,5-dimethylpyrazine; 3,5-dimethyl-2-methylpropylpyrazine, and combinations thereof.

In some embodiments, the at least one hydroxy ketone can comprise acetoin and the at least one substituted pyrazine can be tetramethylpyrazine. In various embodiments, the at least one hydroxy ketone can comprise 1-hydroxy-2-butanone and the at least one substituted pyrazine can be selected from the group consisting of: 2,6-diethylpyrazine; 2,5-diethylpyrazine; 2-ethyl-3,5,6-trimethylpyrazine; 3,5di-methyl-2-(n-propyl)pyrazine; 3,6-dimethyl-2-(n-propyl) pyrazine; 2,5-diethyl-3-methylpyrazine; 2,3-diethyl-5-methylpyrazine; 2,3-diethyl-5,6-dimethylpryazine; trans-3-methyl-2-(n-propyl)-6-(butenyl)pyranzine; ; 2,5-dimethyl-3-ethylpyrazine; and combinations thereof.

In various embodiments of the present invention, the method can further include adding free amino acids to the reaction solution comprising at least one alpha-hydroxy ketone and at least one nitrogen source. In some embodiments, the method can further include adding at least one aldehyde to the reaction solution comprising at least one alpha-hydroxy ketone and at least one nitrogen source.

In various embodiments of the present invention, a method of forming pyrazines is provided, the method comprising receiving a carbon source solution comprising at least one sugar and at least one buffer such that an optimized amount of at least one hydroxy ketone is provided from the at least one sugar, mixing the carbon source solution with at least nitrogen source to form a reaction solution, and heating the reaction solution to a reaction temperature and holding the reaction solution at the reaction temperature for a time sufficient to produce a reaction product comprising at least one substituted pyrazine. Various embodiments of the methods herein can further comprise isolating the at least one substituted pyrazine from the reaction product. The at least one sugar can be selected from the group consisting of glucose, fructose, rhamnose, and combinations thereof. In certain embodiments, the buffer can be selected from the group consisting of: sodium hydroxide, a phosphate buffer, and combinations thereof. In certain embodiments, the buffer can buffer in a pH range of about 6.5 to about 7.5. Methods of the present invention can further comprise adding ammonium ions to the reaction solution comprising a carbon source comprising at least one sugar and at least one buffer.

BRIEF DESCRIPTION OF THE DRAWINGS

In order to provide an understanding of embodiments of the invention, reference is made to the appended drawings, which are not necessarily drawn to scale, and in which reference numerals refer to components of exemplary embodiments of the invention. The drawings are exemplary only, and should not be construed as limiting the invention.

DETAILED DESCRIPTION

Figure 1:
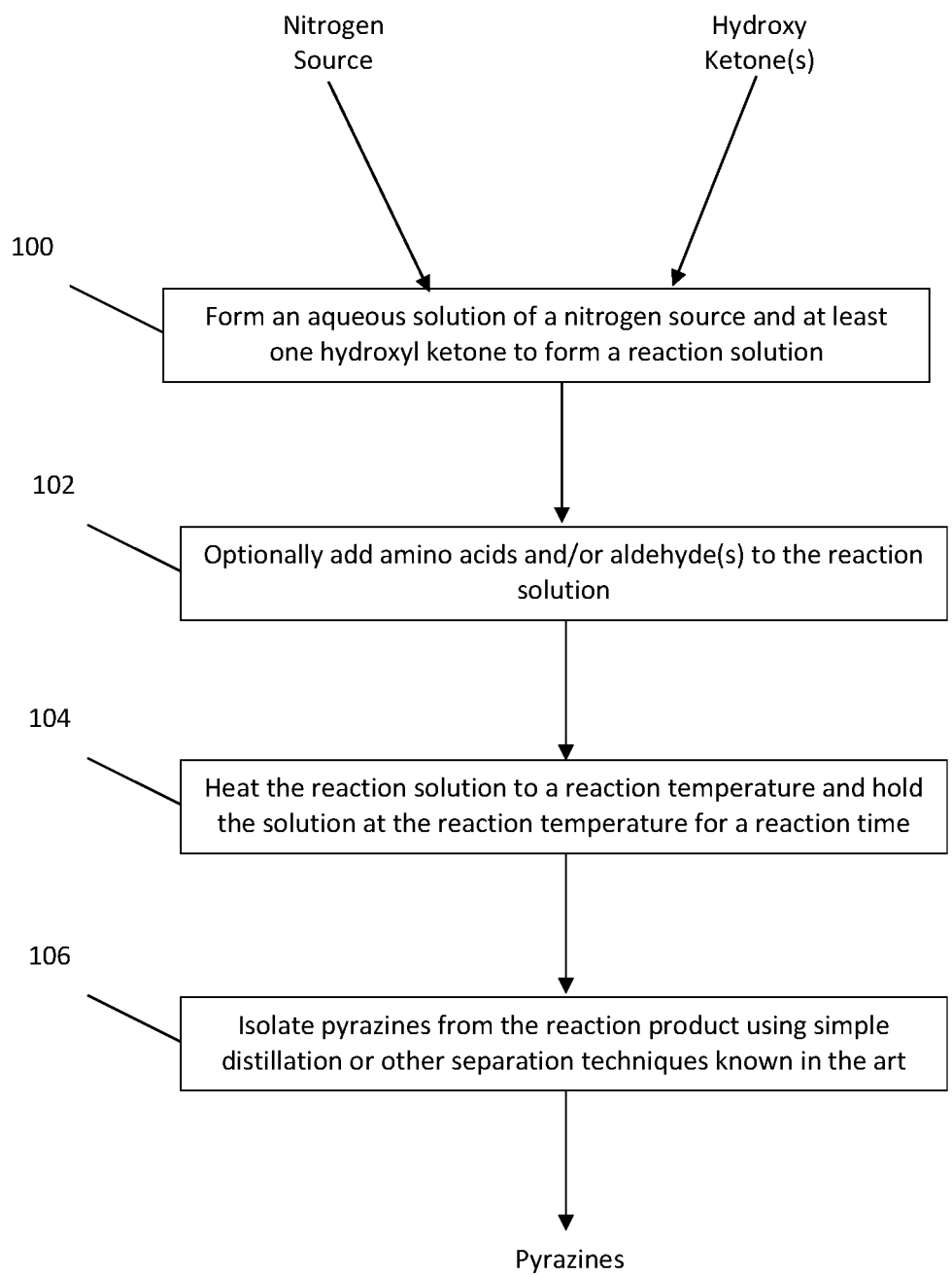
FIG. 1 is a flow chart describing methods of selectively forming substituted pyrazines.

The present invention now will be described more fully hereinafter. This invention may, however, be embodied in many different forms and should not be construed as limited to the embodiments set forth herein; rather, these embodiments are provided so that this disclosure will be thorough and complete, and will fully convey the scope of the invention to those skilled in the art. As used in this specification and the claims, the singular forms "a," "an," and "the" include plural referents unless the context clearly dictates otherwise. Reference to "dry weight percent" or "dry weight basis" refers to weight on the basis of dry ingredients (i.e., all ingredients except water).

The present invention provides methods of forming selected pyrazines. Pyrazines display many different flavor profiles, including, but not limited to, roasted, toasted and nutty notes. For example, pyrazines with cyclopentyl derivatives are known for their positive sensory attributes at very low levels, ppb. Pyrazines are formed by heating mixtures of carbon sources and nitrogen sources. Methods of the present invention not only minimize the formation of the molecules pyrazine and methylpyrazine, but also tailor the reaction so that other desired substituted pyrazines can be produced in a controlled fashion.

Selective Formation of Pyrazines Using a Carbon Source Other than Sugar(s)

Conventionally, sugar(s) have been used as the carbon source in reactions to form pyrazines. Several reaction pathways are known in the art to produce pyrazine-rich formulations using sugar(s), including: 1) hydrolysis of protein into free amino acids followed by reaction of those free amino acids with sugar(s) such as glucose and/or high fructose syrup; and 2) biotechnical synthesis of free amino acids employing glucose and nitrogen (e.g., ammonium ions) followed by reaction of these free amino acids with sugar(s) such as glucose and/or high fructose syrup. When sugars are employed as an intact molecule and reacted with a nitrogen source (e.g., ammonium hydroxide, amino acids), an array of pyrazines are produced, including the molecules pyrazine and methylpyrazine as the dominate pyrazines, with much lesser amounts of dimethylpyrazines, and significantly less amounts of higher molecular weight pyrazines.

As used herein, the term "the molecule pyrazine" refers to a heterocyclic organic compound with the chemical formula $C_4H_4N_2$. This is different from the general term "pyrazine(s)" used herein, which refers to the group of compounds produced from the reaction of a carbon source with a nitrogen source.

As used herein, the term "nitrogen source" refers to a nitrogen containing compound that is reactive with a carbon source to form at least one pyrazine. In various embodiments, a nitrogen source can comprise ammonium ions ($NH_4^+$), amino acids, proteins, or a combination thereof. In some embodiments, ammonium ions ($NH_4^+$) can be provided by compounds such as ammonium hydroxide, diammonium phosphate (DAP), etc. Amino acids can be derived from hydrolysis of protein, for example. In some embodiments, Amino acids can be derived from hydrolysis of tobacco-derived protein, as discussed in U.S. patent application Ser. No. 15/009,199 to Dube et al. filed Jan. 28, 2016, which is herein incorporated by reference in its entirety. Other compounds containing nitrogen that are known in the art and are reactive with a carbon source to form at least one pyrazine can also be used as nitrogen sources in embodiments of the invention disclosed herein.

In various embodiments of the present invention, the carbon source can comprise a hydroxy ketone. A hydroxy ketone is a functional group of a ketone flanked by a hydroxyl group. In two main classes of hydroxy ketones, the hydroxyl group can be placed in the alpha position (i.e., an alpha-hydroxy ketone having the formula RCR'(OH)(CO)R), or in the beta position (i.e., a beta-hydroxy ketone having the formula RCR'(OH)CR$_2$(CO)R). The structures of alpha and beta hydroxy ketones are illustrated below.

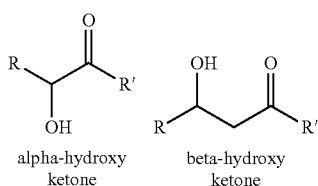

alpha-hydroxy ketone    beta-hydroxy ketone

In various embodiments of the present invention, the carbon source can comprise at least one alpha-hydroxy ketone. In various embodiments of the present invention, R and R' functional groups of the at least one hydroxy ketone can be H or a substituent independently selected from the group consisting of halo (e.g., Cl, F, or Br), OH, optionally substituted C1-10 alkyl, optionally substituted C1-10 alkoxy, optionally substituted C2-4 alkenyl, optionally substituted C2-4 alkynyl, $NR_6R_7$, $NR_6COR_7$, $NR_6CO_2R_7$, $CR_6R_7OR_8$, $CONR_6R_7$, $CO_2R_6$, CN, $CF_3$, $NO_2$, $N_3$, C1-3 alkylthio, $R_9SO$, $R_9SO_2$, $CF_3S$, and $CF_3SO_2$. In certain embodiments of the present invention, R and/or R' functional groups are a C1-6 alkyl.

The term "alkyl" as used herein means saturated straight, branched, or cyclic hydrocarbon groups (i.e., cycloalkyl groups), as well as unsaturated versions of the saturated examples (e.g., propenyl). In particular embodiments, alkyl refers to groups comprising 1 to 10 carbon atoms ("C1-10 alkyl"). In further embodiments, alkyl refers to groups comprising 1 to 8 carbon atoms ("C1-8 alkyl"), 1 to 6 carbon atoms ("C1-6 alkyl"), or 1 to 4 carbon atoms ("C1-4 alkyl"). In other embodiments, alkyl refers to groups comprising 3-10 carbon atoms ("C3-10 alkyl"), 3-8 carbon atoms ("C3-8 alkyl"), or 3-6 carbon atoms ("C3-6 alkyl"). In specific embodiments, alkyl refers to methyl, trifluoromethyl, ethyl, propyl, isopropyl, cyclopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl.

"Optionally substituted" in reference to a substituent group refers to substituent groups optionally substituted with one or more moieties selected from the group consisting of, for example, halo (e.g., Cl, F, Br, and I); alkyl (e.g., C1-10 alkyl), halogenated alkyl (e.g., $CF_3$, 2-Br-ethyl, $CH_2F$, $CH_2Cl$, $CH_2CF_3$, or $CF_2CF_3$); C2-4 alkenyl, C2-4 alkynyl; hydroxyl; amino; amido; carboxylate; carboxamido; carbamate; carbonate; urea; acetate; alkylamino; arylamino; C1-10 alkoxy; aryl; aralkyl, aryloxy; nitro; azido; cyano; thio; alkylthio; sulfonate; sulfide; sulfinyl; sulfo; sulfate; sulfoxide; sulfamide; sulfonamide; phosphonic acid; phosphate; and/or phosphonate.

The term "alkenyl" as used herein means alkyl moieties wherein at least one saturated C—C bond is replaced by a double bond. In particular embodiments, alkenyl refers to groups comprising 2 to 10 carbon atoms ("C2-10 alkenyl"). In further embodiments, alkenyl refers to groups comprising 2 to 8 carbon atoms ("C2-8 alkenyl"), 2 to 6 carbon atoms ("C2-6 alkenyl"), or 2 to 4 carbon atoms ("C2-4 alkenyl"). In specific embodiments, alkenyl can be vinyl, allyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, or 5-hexenyl.

The term "alkynyl" as used herein means alkyl moieties wherein at least one saturated C—C bond is replaced by a triple bond. In particular embodiments, alkynyl refers to groups comprising 2 to 10 carbon atoms ("C2-10 alkynyl"). In further embodiments, alkynyl refers to groups comprising 2 to 8 carbon atoms ("C2-8 alkynyl"), 2 to 6 carbon atoms ("C2-6 alkynyl"), or 2 to 4 carbon atoms ("C2-4 alkynyl"). In specific embodiments, alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl.

The term "alkoxy" as used herein means straight or branched chain alkyl groups linked by an oxygen atom (i.e., —O-alkyl), wherein alkyl is as described above. In particular embodiments, alkoxy refers to oxygen-linked groups comprising 1 to 10 carbon atoms ("C1-10 alkoxy"). In further embodiments, alkoxy refers to oxygen-linked groups comprising 1 to 8 carbon atoms ("C1-8 alkoxy"), 1 to 6 carbon atoms ("C1-6 alkoxy"), 1 to 4 carbon atoms ("C1-4 alkoxy") or 1 to 3 carbon atoms ("C1-3 alkoxy").

The term "halo" or "halogen" as used herein means fluorine, chlorine, bromine, or iodine.

The term "amino" as used herein means a moiety represented by the structure $NR_2$, and includes primary amines, and secondary and tertiary amines substituted by alkyl or aryl (i.e., alkylamino or arylamino, respectively). Thus, $R_2$ may represent two hydrogen atoms, two alkyl moieties, two aryl moieties, one aryl moiety and one alkyl moiety, one hydrogen atom and one alkyl moiety, or one hydrogen atom and one aryl moiety.

Alkyl (amino) is a moiety represented by the structure —RNR$_2$ and includes an alkyl group as defined above attached to an amino group as defined above, wherein the moiety is attached to another portion of a molecule via the alkyl group.

The term "cycloalkyl" means a non-aromatic, monocyclic or polycyclic ring comprising carbon and hydrogen atoms.

The term "derivative" as used herein means a compound that is formed from a similar, beginning compound by attaching another molecule or atom to the beginning compound. Further, derivatives, according to the invention, encompass one or more compounds formed from a precursor compound through addition of one or more atoms or molecules or through combining two or more precursor compounds.

In one embodiment of the present invention, acetoin has been successfully used as the precursor to make tetramethylpyrazine (TMP). Specifically, acetoin has successfully been reacted with ammonium hydroxide and phosphoric acid (or diammonium phosphate) to yield tetramethylpyrazine (TMP) in essentially quantitative yields (>80% yield) with an accompanying significant degree of purity. The reaction between acetoin and ammonium hydroxide produces almost exclusively TMP with little to no detectable amounts of the molecules pyrazine and methylpyrazine. As used herein, the terms "little to no detectable amounts", "substantially no", and "substantially zero" are used to indicate that the identified compound is present in an amount of less than 1.0% by weight, less than 0.5% by weight, or less than 0.1% by weight, based on the total weight of a reaction product.

Without being limited by theory, the different resulting pyrazines synthesized from the reactions with sugar(s) versus acetoin as the carbon source, surprisingly indicate that the carbon source dictates, to a significant degree, the distribution of pyrazines in reactions between carbon sources and nitrogen sources such as ammonium ions and/or amino acids. In particular, it was surprisingly discovered that using different hydroxy ketones as the carbon source in the reaction to form pyrazines can produce an array of specific substituted pyrazines in a controlled fashion.

In certain embodiments, at least one substituted pyrazine produced according to methods described herein is disubstituted. In some embodiments, at least one substituted pyrazine produced according to methods described herein is trisubstituted. In various embodiments, at least one substituted pyrazine produced according to methods described herein is tetrasubstituted. In various embodiments, at least one substituted pyrazine produced according to methods of the present invention comprises at least one substituent group having 2 or more carbon atoms. In certain embodiments, at least one substituted pyrazine produced according to methods of the present invention comprises at least one substituent group having 3 or more carbon atoms.

In some embodiments, at least one substituted pyrazine produced according to methods described herein is a branched pyrazine. As used herein, the term "branched pyrazine" refers to the inclusion of alkyl groups on the pyrazine ring that are not linear in nature. For example, isobutyl, sec-butyl, and tert-butyl groups instead of the n-butyl group (this similarly applies to propyl and pentyl groups). As described in more detail below, it was surprisingly discovered that by varying the alpha hydroxy ketone, the distribution of the pyrazines produced can be dictated. For example, use of acetoin in the reaction yields only tetramethylpyrazine (about 99.5% or greater pure). Use of acetol in the reaction yields mostly dimethylsubstituted pyrazines (about 95% or greater of the yield of pyrazines).

As illustrated in FIG. 1, for example, heated formulations comprising nitrogen sources and at least one hydroxy ketone can produce pyrazines. Pyrazine rich solutions can be prepared in various ways. For example, one method can involve microwave heat treatment of a solution comprising at least one amino acid and at least one hydroxy ketone. As illustrated at operation 100 of FIG. 1, for example, an aqueous reaction solution comprising at least one amino acid and at least one hydroxy ketone can be formed. As illustrated at operation 104 of FIG. 1, for example, the reaction solution can be heated to a reaction temperature and held at the reaction temperature for a reaction time which is sufficient to allow the reactions to undergo a reaction to form pyrazines. As illustrated at operation 106 of FIG. 1, for example, pyrazines can then be optionally isolated from the reaction product using simple distillation or other separation techniques known in the art.

In one embodiment, pyrazines are isolated from the reactant product by first using simple distillation to provide a distillate comprising mostly water and pyrazines. This distillate can then be subjected to liquid liquid extraction with cyclohexane. The amount of cyclohexane used in the liquid liquid extraction can be equal to about half the amount of the distillate used. For example, if 10 L of distillate is used, 5 L of cyclohexane can be used. The liquid liquid extraction of the distillate with cyclohexane can be repeated multiple times. In some embodiments, the liquid liquid extraction of the distillate with cyclohexane can be repeated at least 5 times. Following the liquid liquid extraction, the cyclohexane containing the extracted pyrazines can be dried with any drying agent known in the art. For example, sodium sulfate, magnesium hydroxide, and/or molecular sieves can be used to dry the cyclohexane. After drying, the pyrazines can be isolated (i.e., the cyclohexane can be removed) by simple distillation and/or rotary evaporation.

As discussed above, using different hydroxy ketones as the carbon source in the reaction to form pyrazines can produce an array of specific substituted pyrazines. In certain embodiments, the carbon source comprises acetoin. As discussed in more detail in Example 1 below, for example, when acetoin serves as the sole carbon source in reactions with a nitrogen source (e.g., ammonium hydroxide ($NH_4OH$) and phosphoric acid ($H_3PO_4$), diammonium phosphate, etc.) to make pyrazines, the only pyrazine produced is tetramethylpyrazine. Furthermore, branched pyrazines, such as isopropylpyrazine, are not synthesized via the addition of amino acids (such as, for example, leucine or free amino acids from hydrolyzed F1 protein) to a reaction which contains acetoin, $NH_4OH$ and $H_3PO_4$. Heating the reaction at higher temperatures or for longer periods of time does not change the result (i.e., that tetramethylpyrazine (TMP) is the sole pyrazine synthesized from acetoin). Hence, carbon sources other than acetoin can be synthesized if pyrazines other than TMP are desired from this synthetic approach.

In some embodiments, the carbon source can comprise 1-hydroxyacetone (also referred to as 1-OH-acetone, acetol, or 1-hydroxy-2-propanone). Acetol, an alpha-hydroxy ketone, is the simplest hydroxy ketone. As discussed in more detail below, acetol can be produced by the degradation of various sugars. For example, it can be formed as an intermediate in a Maillard reaction (i.e., reaction of sugar(s) and amino acid(s) to form pyrazines), and then the acetol can react further to form other compounds. In some embodiments of the present invention, the carbon source can comprise 1-hydroxy-2-butanone. The structures of 1-OH-acetone and 1-OH-2-butanone appear below. It is noted that for 1-OH-acetone, a methyl group is bound to one side of the carbonyl and for 1-OH-2-butanone, an ethyl group is bound to one side of the carbonyl. Without being limited by theory, these structural features of the two α,β-hydroxyketones can dictate the structure of the resulting pyrazines.

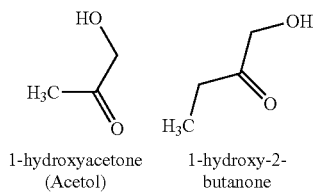

1-hydroxyacetone (Acetol)  1-hydroxy-2-butanone

As illustrated in Example 2 below, for example, reaction of 1-hydroxyacetone as a carbon source and NH₄OH as a source of base and nitrogen can produce an array of pyrazines. When 1-hydroxyacetone (acetol) serves as the carbon source, an array of specific alkyl substituted pyrazines can be produced. For example, exemplary pyrazines provided from the reaction of 1-hydroxyacetone with NH₄OH can include: 2,6-dimethylpyrazine; 2,5-dimethylpyrazine; 2-ethyl-5-methylpyrazine; 2-ethyl-6-methylpyrazine; 2,3,5-trimethylpyrazine; 2-ethyl-3,5-dimethylpyrazine; 2-ethyl-2,5-dimethylpyrazine; 2,3,5,6-tetramethylpyrazine; 2,3,5-trimethyl-6-ethylpyrazine; 2,6-dimethyl-3-propylpyrazine; 2,5-diethyl-3,6-dimethylpyrazine; 2,6-dimethyl-3-(2-methylbutyl)pyrazine; 2,5-dimethyl-3-(2-methylbutyl)pyrazine; 2,5-dimethyl-3-(3-methylbutyl)pyrazine; 2,5-dimethyl-3-propylpyrazine; 2,5-dimethyl-3-cis-propenylpyrazine; 2-isopropenyl-3,6-dimethylpyrazine; 2-(2-methylpropyl)-3,5-dimethylpyrazine; 2,6-dimethyl-3-isobutylpyrazine; 2-(2-methylpropyl)-3,5,6-trimethylpyrazine, 2,3-dimethylpyrazine; trimethylpyrazine; 2,5-dimethyl-3-ethylpyrazine; tetramethylpyrazine; 2,3-diethyl-5-methylpyrazine; 2,5-dimethyl-3-propenylpyrazine; 2,3,5-trimethyl-6-isopropylpyrazine; 2-acetyl-4,5-dimethylpyrazine; and 3,5-dimethyl-2-methylpropylpyrazine.

When 1-hydroxy-2-butanone is used as the sole carbon source, pyrazines having ethyl groups attached can be produced. For example, as illustrated in Example 4 below, pyrazines synthesized from a reaction using 1-OH-2 Butanone and NH4OH can include 2,6-diethylpyrazine; 2,5-diethylpyrazine; 2-ethyl-3,5,6-trimethylpyrazine; 3,5 -dimethyl)-2-(n-propyl)pyrazine; 3,6-dimethyl-2-(n-propyl)pyrazine; 2,5-diethyl-3-methylpyrazine; 2,3-diethyl-5,6-dimethylpryazine; trans-3-methyl-2-(n-propyl)-6-(butenyl)pyrazine; and 2,5-dimethyl-3-ethylpyrazine.

When 1-hydroxyacetone (acetol), 2-hydroxy-3-butanone (acetoin), and 1-hydroxy-2-butanone are used as carbons sources in reactions with nitrogen sources, the pyrazine and methylpyrazine molecules do not appear in the array of structures and pyrazines produced. It is noted that other hydroxy ketones can be used to produce alternative arrays of pyrazine. Using different hydroxy ketones as the carbon source in a reaction to produce pyrazines can not only minimize the formation of pyrazine and methylpyrazine, but also allows one to tailor the reaction so that other desired substituted pyrazines are produced in a controlled fashion.

As illustrated in FIG. 1 at operation 102 for example, amino acids and/or aldehydes can optionally be added to the reaction solution comprising at least one hydroxy ketone and a nitrogen source. As illustrated in Example 3 below, for example, addition of amino acids or selected aldehyde(s) can increase not only the number of synthesized pyrazines, but also can increase the yield of pyrazines. For example, in certain embodiments the reaction solution can comprise an amino acid selected from the group consisting of serine, alanine, leucine, isoleucine, valine, threonine, phenylalanine, and combinations thereof. Similarly, any alkyl aldehyde can be employed to increase the number of synthesized pyrazines as well as the yield of pyrazines. For example, in certain embodiments the reaction solution can comprise an alkyl aldehyde selected from the group consisting of acetaldehyde, propanal, isopropanol, butanal, isobutanal, sec butanal, and combinations thereof.

Increased reaction time and temperature can produce increased pyrazines yield up to the point where a black tar substance is produced. Reaction temperature can be about 30° C. or greater, about 90° C. or greater, about 100° C. or greater, about 120° C. or greater, or about 140° C. or greater for example. In some embodiments, the reaction temperature can be about 90° C. to about 150° C., or about 120° C. to about 140° C. Reaction time can be about 4 hours or greater, 8 hours or greater, about 12 hours or greater, 16 hours or greater, or about 24 hours or greater, for example. In various embodiments, the reaction time can be about 4 to about 24, or about 12 to about 20 hours. In certain embodiments, the reaction time can be about 16 hours.

In various embodiments, the molar ratio of the hydroxy ketone to the nitrogen source can affect the yield of pyrazines. The molar ratio of hydroxy ketone:nitrogen source (e.g., NH₄OH) can be about 1:0.5, about 1:1, about 1:2, or about 1:2.5, for example. In certain embodiments, the ratio of hydroxy ketone to nitrogen source can be between about 1:0.5 to about 1:2.5, or between about 1:1 to about 1:2. In certain embodiments, the ratio of hydroxy ketone to nitrogen source can be about 1:2.

Increasing the pH of the reaction solution can also result in increased amounts of pyrazines. A favored pH range can be about 7.5 to about 10.5, or about 8.5 to about 9.5. In some embodiments, the pH of the reaction solution can be about 8.0 or greater, about 8.5 or greater, about 9.0 or greater or about 10.0 or greater. A small addition of NaOH or KOH, for example, can be used to increase the pH of the reaction solution.

Selective Formation of Pyrazines Using Sugar(s) as the Carbon Source

In various embodiments of the present invention, the selective formation of substituted pyrazines has been optimized using at least one sugar (e.g., glucose, high fructose tobacco syrup (HFTS)) as the carbon source and ammonium ions, protein and/or amino acids as the nitrogen source. As discussed above, various reaction pathways to pyrazine-rich formulations have been previously used to make pyrazines using a sugar as a carbon source. See, e.g., U.S. patent application Ser. No. 15/009,199 to Dube et al., filed Jan. 28, 2016, which is herein incorporated by reference in its entirety. However, when sugars are used as the sole source in the reaction with a nitrogen source (e.g., ammonium hydroxide) to produce pyrazines, the molecules pyrazine and methylpyrazine can be the dominant pyrazines produced. Even when free amino acids are employed as co-reagents, this trend is evident. It was surprisingly discovered that by adjusting the pH of the carbon source before introducing it to the nitrogen source, substituted pyrazines can be selectively produced.

Figure 2:
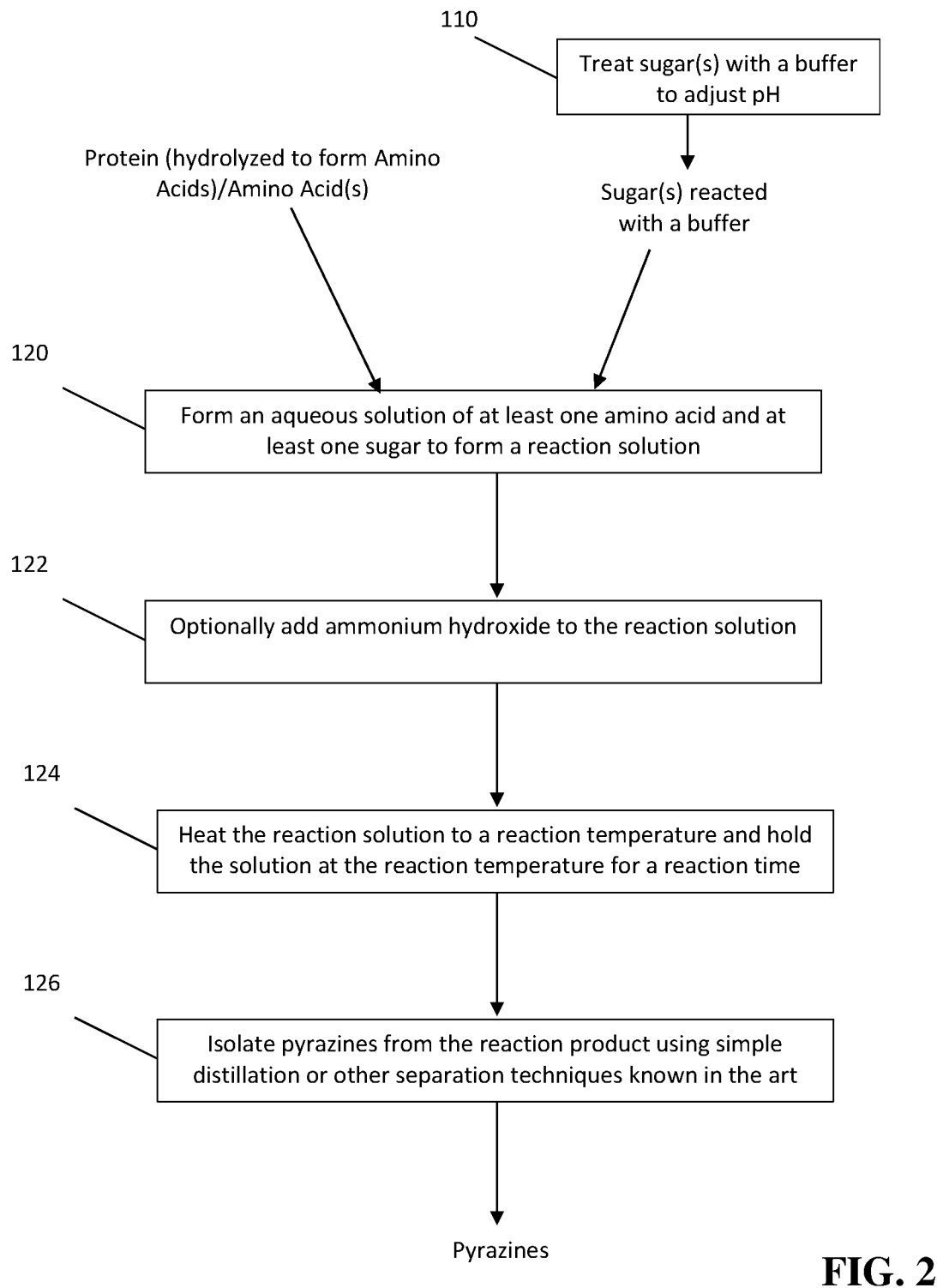
FIG. 2 is a flow chart describing methods of selectively forming substituted pyrazines.

As illustrated in FIG. 2, for example, heated formulations comprising amino acids and sugars can produce pyrazines. See, e.g., U.S. Pat. Pub. No. 2010/0037903 to Coleman III et al.; and Coleman III, On the synthesis and characteristics of aqueous formulations rich in pyrazines, in Flavor Fragrance and Odor Analysis, Second Edition, Ray Marsili, ed., Chapter 7, pp 135-182, CRC Press, Boca Raton, 2012; which are herein incorporated by reference in their entireties. Pyrazine rich solutions can be prepared in various ways. For example, one method can involve microwave heat treatment of a solution comprising at least one amino acid and at least one sugar. As illustrated at operation 120 of FIG. 2, for example, an aqueous reaction solution comprising at least one amino acid and at least one sugar can be formed. As illustrated at operation 124 of FIG. 1, for example, the reaction solution can be heated to a reaction temperature and held at the reaction temperature for a reaction time which is sufficient to allow the reactions to undergo a reaction to form pyrazines.

As discussed above, acetol, a hydroxy ketone, can be produced by the degradation of various sugars. Furthermore, when used as a carbon source in reactions with a nitrogen source, an array of substituted pyrazines can be produced, which do not include the molecules pyrazine and methylpyrazine. Accordingly, acetol can be a key intermediate in the reactions between sugar(s) and free amino acids and/or ammonium ions to make pyrazines containing branched alkyl side chains.

Literature indicates that 1-hydroxy-2-propanone (acetol) can be produced from a C6 sugar such as glucose and a derivative of glucose, sorbitol. See, e.g., M. H. Mohamad, et. al., "A review of acetol: application and production", Amer. J. Appl. Sci., 8, 1135-1139 (2011); M. A. Dasari, "Catalytic conversion of glycerol and sugar alcohols to value added products", Univ. Missouri-Columbia, ISBN-10, 0549727582, pp, 264; W. Yan, "Gas phase conversion of sugars to C3 chemicals, PhD Thesis, University of Missouri-Columbia, 2008; J. Hayami, Mechanism of acetol formation", Bull. Chem. Soc. Japan, 34, 927-932(1961); P. F. Shaw, et. al., "Base catalyzed fructose degradation", J. Agric. Food Chem., 16, 979-982(1968); H. Weenen and W. Apeldoon, "Carbohydrate Cleavage in the Maillard Reaction", Flavor Science, Recent Developments, A. Taylor and D. Mottran, eds., Royal Society of Chemistry, Special Publication #197, Cambridge, 1996; each of which are herein incorporated by reference in their entireties. These references report on the conversion of sugars to 1-hydroxy-2-propanone using phosphate buffers at elevated temperatures, a strong base such as NaOH at pH 11.5 while under reflux, Ni and Palladium catalysts under hydrogen pressure, and copper chromite catalysts in the gas phase of heterogeneous reactions. Copper-chromite has been considered to be the best catalyst. For most of the reactions, the conversion of substrates was greater than 91%. The yield of acetol when they used glycerol as carbon source was 32.2% at 220° C. When sorbitol was used as a carbon source, the highest yield was 11.8% at 280° C. and when glucose was used as a carbon source, the highest yield of acetol was 8.99% at 280° C.

Cellulose has been converted to acetol with a 30% yield using a Sn based catalyst system. See, e.g., F. Chambon, et. al., Process for transformation of lignocellulose biomass or cellulose by catalysts based on Sn oxide and/or Sb oxide and a metal that is selected from Groups 8 to 11, US Patent Application, US2013/028174A1, 2013, which is herein incorporated by reference in its entirety.

Recently Novotny et al., (Czech J. Food Sci., 25, 119-130, 2007, which is herein incorporated by reference) synthesized α-hydroxycarbonyl and α-dicarbonyl compounds via the degradation of monosaccharides. They used three different models comprised of an aqueous solution of potassium peroxodisulfate, an alkaline solution of potassium peroxodisulfate, and a solution of sodium hydroxide, respectively. A total of six α-hydroxycarbonyl and six α-dicarbonyl compounds were identified via GC/MS. The maximum yield of α-dydroxycarbonyl (glycolaldehye, acetol, lactaldehyde, glyceraldehyde, 1,3-dihydroxyacetone and acetoin) when glucose or fructose reacted with sodium hydroxide was approximately 4%. The yield was much lower in the aqueous solutions of potassium peroxodisulfate (0.32%) and alkaline solution of potassium peroxodisulfate (1.1%). Acetol and 1,3-dihydroxyacetone had the highest yield (2.52 and 1.02%, respectively) when sodium hydroxide was used.

As illustrated in Example 6 below, alpha hydroxy ketones (e.g., acetol) can be produced from sugar to ultimately be used as the carbon source in sugar ammonia reactions. The acetol can be isolated via both distillation and column chromatography and then used as a carbon source in the reactions described herein. However, both techniques are time consuming (distillation) and expensive (chromatography). As such, it can be preferable to avoiding having to isolate hydroxy ketones derived from a sugar source before using these hydroxy ketones in reactions with a nitrogen source to produce pyrazines.

As illustrated in Example 7 below, for example, it has been surprisingly discovered that substituted pyrazines can be selectively formed from a sugar carbon source without first isolating a hydroxy ketone (e.g., acetol, acetoin, etc.) formed from the degradation of the sugar(s). As illustrated at operation 110 of FIG. 2, for example, by treating the sugar(s) with a buffer before combining the sugar(s) with the nitrogen source, a different array of pyrazines can be produced than the array of pyrazines produced from the reaction of sugar(s) that were not pre-treated with a buffer and a nitrogen source. The reactions can be optimized such that the maximum amount of acetol and acetol-like compounds are produced from the sugar carbon source. Without being limited by theory, the role of the buffer is to control the pH so that the maximum amount of hydroxy ketone(s) (e.g., acetol, acetoin, etc.) are produced from the degradation of the sugar.

In some embodiments, the buffer can be a sodium hydrogen phosphate/sodium hydroxide buffer with a pH of about 12. In various embodiments, the buffer can include a potassium phosphate buffer with a pH of about 6.5 to about 7.5. In certain embodiments, the buffer can include sodium carbonate, sodium sulfite, peroxodisulfate, sodium phosphate, or combinations thereof. The selection of the buffer type, capacity, pH, and reaction temperature can affect the synthesis of hydroxy ketones from the sugar carbon source, and can therefore impact the array of pyrazines produced as well as the quantity of pyrazines produced from the subsequent reaction with a nitrogen source.

In various embodiments, the buffer can buffer at a pH of approximately neutral or in an alkaline range, such as at a pH greater than about 6, greater than about 8, or greater than about 10 (e.g., about 6 to about 12). For example, in certain embodiments, the pH of the sugar carbon source can be buffered to about 11 to about 12. In some embodiments, the pH of the sugar carbon source can be buffered to about 6.5 to about 7.5.

For example, glucose is a known carbon source for the production of pyrazines. When employed as an intact molecule and reacted with ammonium hydroxide, an array of pyrazines are produced, including the molecules pyrazine and methylpyrazine as the dominate pyrazines with much lesser amounts of dimethylpyrazines and significantly less amounts of higher molecular weight pyrazines. When the glucose is pre-reacted with NaOH at pH 12 followed by reaction with ammonium hydroxide, a very similar array of pyrazines are produced. However, it was surprisingly discovered that if the glucose was treated with a potassium phosphate buffer at pH 6.5 followed by reaction with ammonium hydroxide, only dimethylpyrazines and higher molecular weight pyrazines were produced, thereby excluding the production of the less desirable molecules pyrazine and methylpyrazine.

Increased reaction time between the buffered sugar(s) carbon source and the nitrogen source and temperature can produce increased pyrazines yield up to the point where a black tar substance is produced. Reaction temperature can be about 30° C. or greater, about 90° C. or greater, about 100° C. or greater, about 120° C. or greater, or about 140° C. or greater for example. In some embodiments, the reaction temperature can be about 90° C. to about 150° C., or about 120° C. to about 140° C. Reaction time can be about 30 mins or greater, about 60 mins or greater, about 90 mins or greater, or about 120 mins or greater, for example. In various embodiments, the reaction time can be about 30 mins to about 150 mins, or about 60 mins to about 120 mins.

Increasing the pH of the reaction solution can also result in increased amounts of pyrazines. A favored pH range can be about 7.5 to about 10.5, or about 8.5 to about 9.5. In some embodiments, the pH of the reaction solution can be about 8.0 or greater, about 8.5 or greater, about 9.0 or greater or about 10.0 or greater. A small addition of NaOH or KOH, for example, can be used to increase the pH of the reaction solution.

In various embodiments of the present invention, as illustrated at operation 122 of FIG. 2 for example, the addition of $NH_4OH$ to the amino acid/sugar reaction solution can increase the yield of pyrazines. The $NH_4OH$/sugar molar ratio can have a dramatic influence on the yield of pyrazines. For example, a molar ratio of sugar to $NH_4OH$ of about 6:1 to about 1:1, or about 5:1 to about 2:1 (e.g., about 5:1, about 2.5:1, about 2:1, or about 1.5:1), followed by heat treatment can produce formulations rich in pyrazines. In some embodiments, aqueous $NH_4OH$ can slowly be added into the amino acid/sugar solution over the course of the reaction.

Different sugars and amino acids affect the types of pyrazines formed. See, e.g., Coleman and Steichen, 2006, Sugar and selected amino acid influences on the structure of pyrazines in microwave heat treated formulations, J. Sci. Food Agric., 86, 380-391, which is herein incorporated by reference in its entirety. For example, leucine and valine produce more branched pyrazines with highly substituted subchains and lower odor thresholds. Highly substituted pyrazines are relatively more potent than pyrazines that are not as branched, and therefore can be desirable in some applications. The substitution in the pyrazine can be a result of the amino acid used in the reaction. Therefore, it can be advantageous to select amino acids with branching, highly substituted subchains. With regard to sugars, rhamnose can be an ideal sugar for pyrazine formation, followed by fructose and then glucose.

As illustrated at operation 126 of FIG. 2, for example, following the reaction, optionally pyrazines can be isolated from the reaction product using simple distillation, rotary evaporation, or other separation techniques known in the art. In certain embodiments, rotary evaporation can be a preferred isolation technique in a scaled up process of deriving tobacco-derived pyrazines.

Uses of Substituted Pyrazines in Tobacco Products

As described above, pyrazines generated according to the present invention can be useful as components (e.g., flavorants) incorporated into tobacco products, for example. The tobacco product to which the materials of the invention are added can vary, and can include any product configured or adapted to deliver tobacco or some component thereof to the user of the product. Exemplary tobacco products include smoking articles (e.g., cigarettes), smokeless tobacco products, and aerosol-generating devices that contain a tobacco material or other plant material that is not combusted during use.

Figure 6:
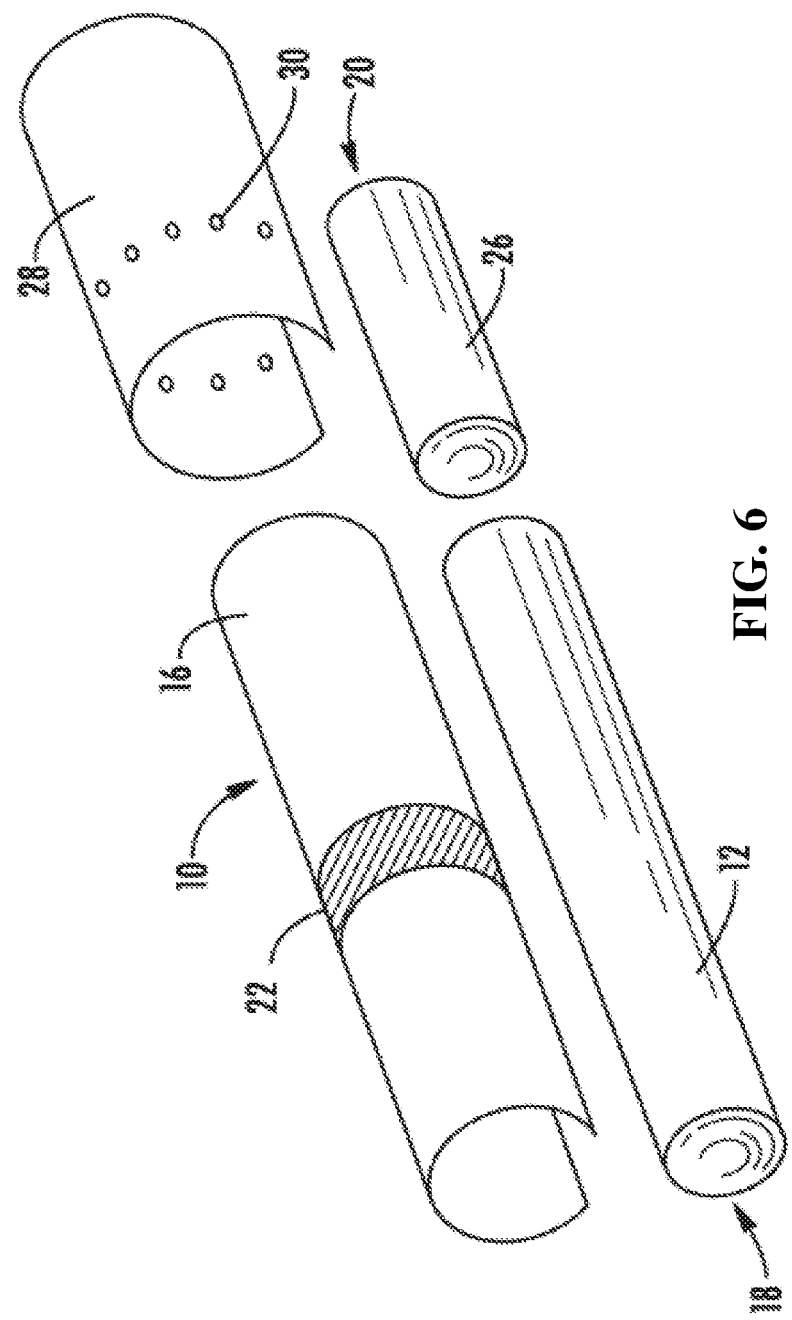
FIG. 6 is an exploded perspective view of a smoking article having the form of a cigarette, showing the smokable material, the wrapping material components, and the filter element of the cigarette.

In various embodiments of the present invention, pyrazines can be incorporated into smoking articles in the form of a flavorant in a tobacco composition and/or in a filter element of a smoking article. For example, pyrazines can be incorporated into a top dressing or casing of a tobacco product. Referring to FIG. 6, there is shown a smoking article 10 in the form of a cigarette and possessing certain representative components of a smoking article that can contain products derived from the cellulosic sugar materials of the present invention. The cigarette 10 includes a generally cylindrical rod 12 of a charge or roll of smokable filler material (e.g., about 0.3 to about 1.0 g of smokable filler material such as tobacco material) contained in a circumscribing wrapping material 16. The rod 12 is conventionally referred to as a "tobacco rod." The ends of the tobacco rod 12 are open to expose the smokable filler material. The cigarette 10 is shown as having one optional band 22 (e.g., a printed coating including a film-forming agent, such as starch, ethylcellulose, or sodium alginate) applied to the wrapping material 16, and that band circumscribes the cigarette rod in a direction transverse to the longitudinal axis of the cigarette. The band 22 can be printed on the inner surface of the wrapping material (i.e., facing the smokable filler material), or less preferably, on the outer surface of the wrapping material.

At one end of the tobacco rod 12 is the lighting end 18, and at the mouth end 20 is positioned a filter element 26. The filter element 26 positioned adjacent one end of the tobacco rod 12 such that the filter element and tobacco rod are axially aligned in an end-to-end relationship, preferably abutting one another. Filter element 26 may have a generally cylindrical shape, and the diameter thereof may be essentially equal to the diameter of the tobacco rod. The ends of the filter element 26 permit the passage of air and smoke therethrough. A plug wrap 28 enwraps the filter element and a tipping material (not shown) enwraps the plug wrap and a portion of the outer wrapping material 16 of the rod 12, thereby securing the rod to the filter element 26.

The filter element of the invention typically comprises multiple longitudinally extending segments. Each segment can have varying properties and may include various materials capable of filtration or adsorption of particulate matter and/or vapor phase compounds. Typically, the filter element of the invention includes 2 to 6 segments, frequently 2 to 4 segments. In one preferred embodiment, the filter element includes a mouth end segment, a tobacco end segment and a compartment therebetween. This filter arrangement is sometimes referred to as a "compartment filter" or a "plug/space/plug" filter. The compartment may be divided into two or more compartments as described in greater detail below.

In various embodiments, the filter element can comprise an adsorbent in the form of an activated carbon material, wherein the activated carbon is capable of removing at least one gas phase component of mainstream smoke is incorporated into the filter element. In certain embodiments, the filter element 26 can include ventilation holes 30 that extend through the tipping paper (not shown) and the plug wrap 28 and, thus, provide air dilution of mainstream smoke. The ventilation holes 30 may be configured as a single line of perforations extending circumferentially around the filter element 26 or may comprise several lines of perforations. As would be understood, the exact count and size of the ventilation holes 30 will vary depending on the desired level of air dilution.

Figure 7:
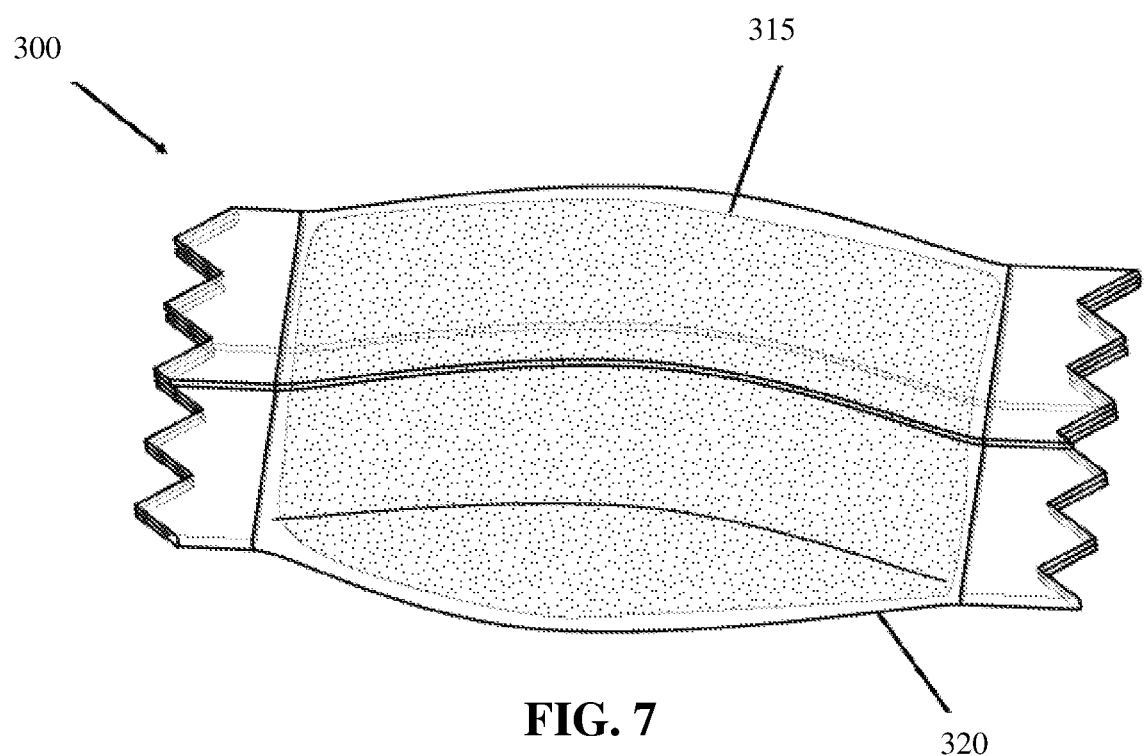
FIG. 7 is a top view of a smokeless tobacco product embodiment, taken across the width of the product, showing an outer pouch filled with a tobacco material.

In various embodiments of the present invention, pyrazines obtained through methods disclosed herein can be incorporated into smokeless tobacco products in the form of a flavorant in a smokeless tobacco formulation. The form of the smokeless tobacco product of the invention can vary. In one particular embodiment, the product is in the form of a snus-type product containing a particulate tobacco material and a flavorant comprising a pyrazine obtained through methods of the present invention. Manners and methods for formulating snus-type tobacco formulations will be apparent to those skilled in the art of snus tobacco product production. For example, as illustrated in FIG. 7, an exemplary pouched product 300 can comprise an outer water-permeable container 320 in the form of a pouch which contains a particulate mixture 315 adapted for oral use. The orientation, size, and type of outer water-permeable pouch and the type and nature of the composition adapted for oral use that are illustrated herein are not construed as limiting thereof.

In various embodiments, a moisture-permeable packet or pouch can act as a container for use of the composition within. The composition/construction of such packets or pouches, such as the container pouch 320 in the embodiment illustrated in FIG. 7, may be varied as noted herein. For example, suitable packets, pouches or containers of the type used for the manufacture of smokeless tobacco products, which can be modified according to the present invention, are available under the tradenames CatchDry, Ettan, General, Granit, Goteborgs Rape, Grovsnus White, Metropol Kaktus, Mocca Anis, Mocca Mint, Mocca Wintergreen, Kicks, Probe, Prince, Skruf and TreAnkrare. A pouch type of product similar in shape and form to various embodiments of a pouched product described herein is commercially available as ZONNIC (distributed by Niconovum AB). Additionally, pouch type products generally similar in shape and form to various embodiments of a pouched product are set forth as snuff bag compositions E-J in Example 1 of PCT WO 2007/104573 to Axelsson et al., which is incorporated herein by reference, which are produced using excipient ingredients and processing conditions that can be used to manufacture pouched products as described herein.

The amount of material contained within each pouch may vary. In smaller embodiments, the dry weight of the material within each pouch is at least about 50 mg to about 150 mg. For a larger embodiment, the dry weight of the material within each pouch preferably does not exceed about 300 mg to about 500 mg.

In some embodiments, each pouch/container can have disposed therein a flavor agent member, as described in greater detail in U.S. Pat. No. 7,861,728 to Holton, Jr. et al., which is incorporated herein by reference. The flavor agent member can comprise a flavorant comprising a pyrazine derived via methods of the present invention, as discussed above. If desired, other components can be contained within each pouch. For example, at least one flavored strip, piece or sheet of flavored water dispersible or water soluble material (e.g., a breath-freshening edible film type of material) may be disposed within each pouch along with or without at least one capsule. Such strips or sheets may be folded or crumpled in order to be readily incorporated within the pouch. See, for example, the types of materials and technologies set forth in U.S. Pat. No. 6,887,307 to Scott et al. and U.S. Pat. No. 6,923,981 to Leung et al.; and The EFSA Journal (2004) 85, 1-32; which are incorporated herein by reference.

In various embodiments, the outer water-permeable pouch can comprise PLA or other pouch materials known in the art. Descriptions of various components of snus types of products and components thereof also are set forth in US Pat. App. Pub. No. 2004/0118422 to Lundin et al., which is incorporated herein by reference. See, also, for example, U.S. Pat. No. 4,607,479 to Linden; U.S. Pat. No. 4,631,899 to Nielsen; U.S. Pat. No. 5,346,734 to Wydick et al.; and U.S. Pat. No. 6,162,516 to Derr, and US Pat. Pub. No. 2005/0061339 to Hansson et al.; each of which is incorporated herein by reference. See, also, the types of pouches set forth in U.S. Pat. No. 5,167,244 to Kjerstad, which is incorporated herein by reference. Snus types of products can be manufactured using equipment such as that available as SB 51-1/T, SBL 50 and SB 53-2/T from Merz Verpackungmaschinen GmBH. Snus pouches can be provided as individual pouches, or a plurality of pouches (e.g., 2, 4, 5, 10, 12, 15, 20, 25 or 30 pouches) can connected or linked together (e.g., in an end-to-end manner) such that a single pouch or individual portion can be readily removed for use from a one-piece strand or matrix of pouches.

The invention is not limited to snus-type smokeless tobacco products. For example, the mixture of tobacco material and flavorants comprising at least one pyrazine derived via the methods described herein can also be incorporated into various smokeless tobacco forms such as loose moist snuff, loose dry snuff, chewing tobacco, pelletized tobacco pieces, extruded tobacco strips or pieces, finely divided or milled agglomerates of powdered pieces and components, flake-like pieces (e.g., that can be formed by agglomerating tobacco formulation components in a fluidized bed), molded tobacco pieces (e.g., formed in the general shape of a coin, cylinder, bean, cube, or the like), pieces of tobacco-containing gum, products incorporating mixtures of edible material combined with tobacco pieces and/or tobacco extract, products incorporating tobacco (e.g., in the form of tobacco extract) carried by a solid inedible substrate, and the like. For example, the smokeless tobacco product can have the form of compressed tobacco pellets, multilayered extruded pieces, extruded or formed rods or sticks, compositions having one type of tobacco formulation surrounded by a different type of tobacco formulation, rolls of tape-like films, readily water-dissolvable or water-dispersible films or strips (see, for example, US Pat. Appl. Pub. No. 2006/0198873 to Chan et al.), or capsule-like materials possessing an outer shell (e.g., a pliable or hard outer shell that can be clear, colorless, translucent or highly colored in nature) and an inner region possessing tobacco or tobacco flavor (e.g., a Newtonian fluid or a thixotropic fluid incorporating tobacco of some form).

In some embodiments, smokeless tobacco products of the invention can have the form of a lozenge, tablet, microtab, or other tablet-type product. See, for example, the types of lozenge formulations and techniques for formulating or manufacturing lozenges set forth in U.S. Pat. No. 4,967,773 to Shaw; U.S. Pat. No. 5,110,605 to Acharya; U.S. Pat. No. 5,733,574 to Dam; U.S. Pat. No. 6,280,761 to Santus; U.S. Pat. No. 6,676,959 to Andersson et al.; U.S. Pat. No. 6,248,760 to Wilhelmsen; and U.S. Pat. No. 7,374,779; US Pat. Pub. Nos. 2001/0016593 to Wilhelmsen; 2004/0101543 to Liu et al.; 2006/0120974 to Mcneight; 2008/0020050 to Chau et al.; 2009/0081291 to Gin et al.; and 2010/0004294 to Axelsson et al.; which are incorporated herein by reference.

Depending on the type of smokeless tobacco product being processed, the tobacco product can include one or more additional components in addition to the tobacco material and the flavorants comprising at least one pyrazine derived from methods of the present invention. For example, the tobacco material and the tobacco-derived flavorants can be processed, blended, formulated, combined and/or mixed with other materials or ingredients, such as other tobacco materials or flavorants, fillers, binders, pH adjusters, buffering agents, salts, sweeteners, colorants, disintegration aids, humectants, and preservatives (any of which may be an encapsulated ingredient). See, for example, those representative components, combination of components, relative amounts of those components and ingredients relative to tobacco, and manners and methods for employing those components, set forth in US Pat. Pub. Nos. 2011/0315154 to Mua et al. and 2007/0062549 to Holton, Jr. et al. and U.S. Pat. No. 7,861,728 to Holton, Jr. et al., each of which is incorporated herein by reference.

In various embodiments, at least one pyrazine derived from methods described herein can be incorporated into smokeless tobacco products in the form of a flavorant in an electronic smoking article. There have been proposed numerous smoking products, flavor generators, and medicinal inhalers that utilize electrical energy to vaporize or heat a volatile material, or attempt to provide the sensations of cigarette, cigar, or pipe smoking without burning tobacco to a significant degree. See, for example, the various alternative smoking articles, aerosol delivery devices and heat generating sources set forth in the background art described in U.S. Pat. No. 7,726,320 to Robinson et al., U.S. Pat. Pub. Nos. 2013/0255702 to Griffith Jr. et al., 2014/0000638 to Sebastian et al., 2014/0060554 to Collett et al., 2014/0096781 to Sears et al., 2014/0096782 to Ampolini et al., and 2015/0059780 to Davis et al., which are incorporated herein by reference in their entirety.

Figure 8:
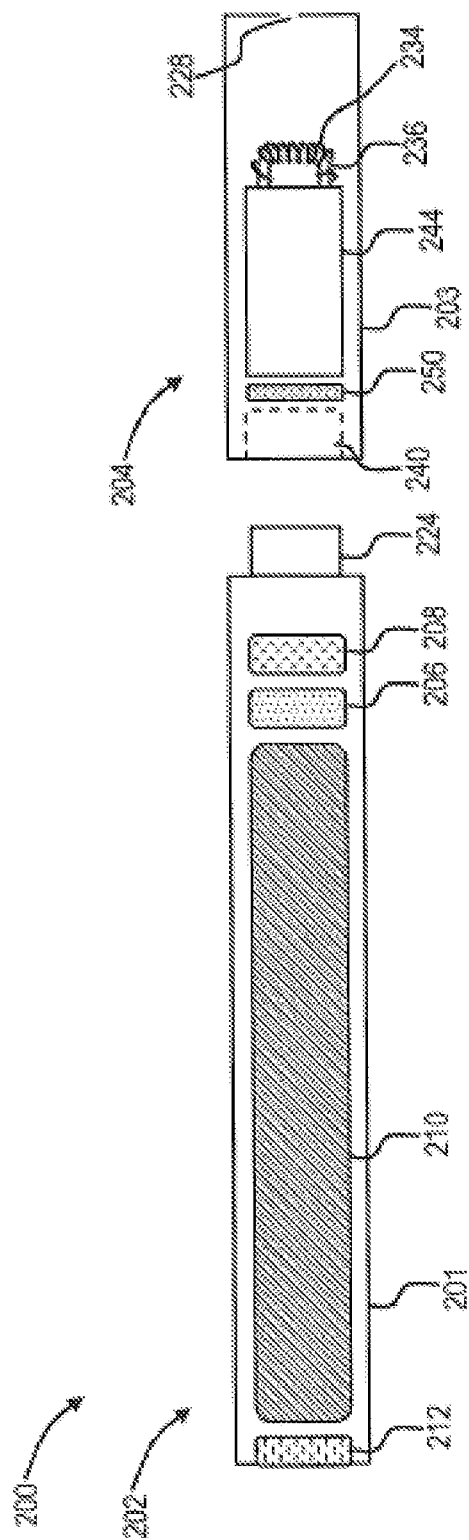
FIG. 8 is a sectional view through an electronic smoking article comprising a cartridge and a control body and including a reservoir housing according to an example embodiment of the present disclosure.

An exemplary embodiment of an electronic smoking article 200 is shown in FIG. 8. As illustrated therein, a control body 202 can be formed of a control body shell 201 that can include a control component 206, a flow sensor 208, a battery 210, and an LED 212. A cartridge 204 can be formed of a cartridge shell 203 enclosing a reservoir housing 244 that is in fluid communication with a liquid transport element 236 adapted to wick or otherwise transport an aerosol precursor composition stored in the reservoir housing to a heater 234. An opening 228 may be present in the cartridge shell 203 to allow for egress of formed aerosol from the cartridge 204. Such components are representative of the components that may be present in a cartridge and are not intended to limit the scope of cartridge components that are encompassed by the present disclosure. The cartridge 204 may be adapted to engage the control body 202 through a press-fit engagement between the control body projection 224 and the cartridge receptacle 240. Such engagement can facilitate a stable connection between the control body 202 and the cartridge 204 as well as establish an electrical connection between the battery 210 and control component 206 in the control body and the heater 234 in the cartridge. The cartridge 204 also may include one or more electronic components 250, which may include an IC, a memory component, a sensor, or the like. The electronic component 250 may be adapted to communicate with the control component 206. The various components of an electronic smoking device according to the present disclosure can be chosen from components described in the art and commercially available.

In various embodiments, the aerosol precursor composition can comprise a flavorant comprising at least one pyrazine derived according to methods of the present invention. Exemplary formulations for aerosol precursor materials that may be used according to the present disclosure are described in U.S. Pat. No. 7,217,320 to Robinson et al.; U.S. Pat. Pub. Nos. 2013/0008457 to Zheng et al.; 2013/0213417 to Chong et al.; 2014/0060554 to Collett et al.; and 2014/0000638 to Sebastian et al., the disclosures of which are incorporated herein by reference in their entirety. Other aerosol precursors that can incorporate the tobacco-derived pyrazines described herein include the aerosol precursors that have been incorporated in the VUSE® product by R. J. Reynolds Vapor Company, the BLU™ product by Imperial Tobacco, the MISTIC MENTHOL product by Mistic Ecigs, and the VYPE product by CN Creative Ltd. Also desirable are the so-called "smoke juices" for electronic cigarettes that have been available from Johnson Creek Enterprises LLC.

EXPERIMENTAL

Aspects of the present invention are more fully illustrated by the following examples, which are set forth to illustrate certain aspects of the present invention and are not to be construed as limiting thereof.

Example 1

Pyrazines are produced using acetoin (3-hydroxy-2-butanone) instead of sugar(s) as the carbon source in reactions with ammonia.

Acetoin, ammonium hydroxide (28-30%), leucine, dichloromethane, and phosphoric acid ($H_3PO_4$) are obtained from Sigma-Aldrich (St. Louis, Mo.). F1 protein is obtained from R. J. Reynolds Tobacco Co. (Winston-Salem, N.C.) and hydrolyzed. The weight percent of hydrolyzed amino acids in all of the hydrolyzed solutions is in the range of 50-55%. All pyrazine synthesis reactions are performed in a 40 mL Parr vessel. In each reaction, 0.8 gram of acetoin is mixed with 1.8 mL of $NH_4OH$ and 0.6 mL of $H_3PO_4$, and then enough hydrolyzed F1 protein (20 mL) is added to make the mass of amino acids equal to 0.4 gram. For example, when 40 grams of F1 protein is hydrolyzed in 1 liter solution, the weight percent of amino acids in the solution is equal to 50%, which is equal to 20 grams of amino acids in 1 liter solution. In order to use 0.4 gram of amino acids in a reaction, only 20 mL of above solution is added to the reaction vessel. In some of the reactions, instead of hydrolyzed F1 protein, leucine is used as a source of amino acid and only 20 mL of water is added to adjust the volume. For all solutions, the pH is adjusted to 8.0 and then reaction is started. After completion of each reaction, the mixture is extracted with 30 mL of dichloromethane (DCM). Next, 200 μL of the DCM extract is diluted to 1 mL using DCM and analyzed via GC/MS.

All GC/MS analyses are performed using a 6890 GC equipped with a 5973 Mass Selective detector (MSD) from Agilent (Wilmington, Del.). Separations are obtained using a DB-WAXTER capillary column (30 m long×250 μm I.D. with a film thickness of 0.25 μm) from J&W (Wilmington, Del.). The following operating parameters are used for each analysis:

| | |
|---|---|
| Injection Port Temp | 260° C. |
| Purge Valve | 3 mL/min |

| | |
|---|---|
| Purge Time | 1 min |
| Total Flow | 24 mL/min |
| Constant Flow | 1 mL/min |
| Injection Volume | 2 μL, split 1:20 |
| Column Oven Initial Temp | 50° C. |
| Column Oven Initial Time | 3 min |
| Column Oven Ramp Rate | 15° C./min |
| Column Oven Final Temp | 250° C. |
| Column Oven Final Time | 1 min |
| MSD Transfer line Temp | 260° C. |

MS Wiley library is used to identify each pyrazine.

In a first reaction, acetoin (0.8 gram) is reacted with $NH_4OH$ (1.8 mL) and $H_3PO_4$ (0.6 mL) at pH=8 at 90° C. for 12-15 hours. More than 90% of acetoin is converted to tetramethylpyrazine (TMP). Next, the reaction is repeated using identical conditions, but instead of heating the reaction at 90° C. for 12-15 hours, it is heated only for 4 hours at 120° C. Results are similar to those obtained at 90° C. and 12-15 hours.

Next, in order to determine if branched pyrazines can be synthesized, an amino acid (leucine) is added to the reaction reagent mixture. For this purpose, 0.8 gram acetoin+1.8 mL of $NH_4OH$+0.6 mL of $H_3PO_4$ and 0.25 gram of leucine are mixed with 20 mL of $H_2O$ and pH is adjusted to 8. Then the reaction is heated for 18 hours at 120° C. and then the reaction mixture is extracted with 30 mL of DCM and analyzed via GC/MS. Only TMP ($t_R$=8.2 min) and some acetoin ($t_R$=6.1 min) are detected. No branched pyrazines are detected.

Next, a similar reaction is performed, but instead of leucine and $H_2O$, 20 mL of hydrolyzed F1 protein is used for the reaction. The reaction is performed in the Parr vessel at 120° C. for 18 hours. After cooling the reactant, 30 mL DCM is used to extract the pyrazines. Again, no branched pyrazines were observed, only TMP.

In order to determine whether ammonia is consuming all the acetoin and thus preventing the amino acid(s) from reacting with acetoin, another source of base (NaOH) is used instead of $NH_4OH$ to assure that basic, pH>8, reaction conditions are maintained. For this purpose, two reactions are performed. In the first reaction, 0.8 acetoin is mixed with 0.25 gram of leucine and 20 mL of 0.1N NaOH (pH=12), while in the second reaction the pH is adjusted to 8.2 using $H_3PO_4$. Both reactions are heated at 120° C. for 8 hours using the Parr vessel. After cooling the reaction, the reactants are extracted with DCM and analyzed via GC/MS. No pyrazines, not even TMP, are detected.

The above reactions illustrate that the addition of amino acids to the reaction of acetoin and $NH_4OH$ does not produce branched pyrazines. Furthermore, it is discovered that acetoin is not a key intermediate in the reactions between sugar(s) and free amino acids to make pyrazines containing branched alkyl side chains.

Example 2

Hydroxy ketone carbon sources other than acetoin are utilized to selectively produce pyrazines other than TMP.

1-OH-acetone, 1-OH-2-butanone, ammonium hydroxide (28-30%), phosphoric acid ($H_3PO_4$), isoleucine, threonine, and isovaleraldehyde are obtained from Sigma-Aldrich (St. Louis, Mo.). F1 proteins derived from a plant of the *Nicotiana* species are obtained from R. J. Reynolds Tobacco Co. (Winston-Salem, N.C.) and hydrolyzed to form amino acids. The weight percent of hydrolyzed amino acids in all of the hydrolyzed solutions are in the range of 50-55%.

All pyrazine synthesis reactions are performed in a 40 mL Parr vessel. In each reaction, 1 gram of 1-OH-acetone or 1-OH-2-butanone is mixed with 0.25, 0.5, 1 and 1.25 mL of $NH_4OH$ and 10 mL of $H_2O$. Each reaction is mixed and heated at different temperatures (100-140° C.) for a period of 4-24 hours. The pH levels for most of the reactions are approximately 11 (no adjustments are made). However, in the reactions in which the pH level is adjusted to 8, concentrated $H_3PO_4$ is used to lower the pH.

After the completion of each reaction, the mixture is extracted with 20-25 mL of dichloromethane. In each extraction, 250 μg of deuterated 2-methylpyrazine is used as an internal standard for all quantifications. For all reactions, the mixtures are stirred using a magnetic stirrer during the reaction process.

All GC/MS analyses are performed using the same equipment and operating parameters as those used in Example 1 above. MS Wiley library is used to identify each pyrazine. For quantitative analysis, pyrazines are quantified using single ion monitoring mode. Each pyrazine is quantified against the mass of internal standard (250 μg) added to the extraction solvent.

Initially, 1-hydroxyacetone is reacted with $NH_4OH$ at different ratios, temperatures, pH levels, and reaction times to maximize the percent yield of pyrazines. The pyrazines detected from the reaction of 1-OH-acetone with $NH_4OH$ include: 2,6-dimethylpyrazine; 2,5-dimethylpyrazine; 2-ethyl-5-methylpyrazine; 2-ethyl-6-methylpyrazine; 2,3,5-trimethylpyrazine; 2-ethyl-3,5-dimethylpyrazine; 2-ethyl-2,5-dimethylpyrazine; 2,3,5,6-tetramethylpyrazine; 2,3,5-trimethyl-6-ethylpyrazine; 2,6-dimethyl-3-propylpyrazine; 2,5-diethyl-3,6-dimethylpyrazine; 2,6-dimethyl-3-(2-Methylbutyl)pyrazine; 2,5-dimethyl-3-(2-MethylButyl)pyrazine; 2,5-dimethyl-3-(3-MethylButyl)pyrazine; 2,5-dimethyl-3-propylpyrazine; 2,5-dimethyl-3-cis-propenylpyrazine; 2-isopropenyl-3,6-dimethylpyrazine; 2-(2-methylpropyl)-3,5-dimethylpyrazine; 2,6-dimethyl-3-isobutylpyrazine; 2-(2-methylpropyl)-3,5,6-trimethylpyrazine.

In a first part of this study, reactions are performed at two different pH levels (8.0 and 11.0) to determine which pH levels provide the highest yield and greatest number of pyrazines. In a first reaction, 1 mL of 1-OH-acetone is reacted with 0.5 mL of $NH_4OH$ and 10 mL of $H_2O$. The pH level for this reaction is measured to be around 11.0. In a second reaction, the same volume of reactant is mixed, but the pH level is adjusted to 8.0 using concentrated $H_3PO_4$. Both reactions are heated at 120° C. for 12 hours. The percent yield of the pyrazines is higher when the pH level is around 11.0. For this purpose, the pH level of later experiments is not adjusted and reactions are performed at pH 11 or higher.

The effects of temperature (100, 110, 120, 130 and 140° C.) on the synthesis of pyrazines using 1-OH-acetone (1 g) and $NH_4OH$ (1 g) with a 1:2 mole ratio of C:N in 10 mL of $H_2O$ (reaction time 12 hours) is texted next. Pyrazine yield increases as the temperature increases, still showing an increase in pyrazine yield as the temperature reached 140° C.

The effect of varying reaction times (4, 8, 12, 16, and 24 hours) on the synthesis of pyrazines using 1-OH-acetone (1 g) and $NH_4OH$ (1 g) with a 1:2 mole ratio of C:N in 10 mL of $H_2O$ is tested. Maximum yields of pyrazines are obtained when the reaction time is 16 hours.

The effect of varying the 1-OH-acetone:$NH_4OH$ molar ratio (1:0.5, 1:1, 1:2, and 1:2.5, 1-OH-acetone and $NH_4OH$)

reaction in 10 mL of $H_2O$ on the yield of pyrazines at 120° C. after 12 hours is tested. The optimum ratio is 1:2, which is equal to 1 gram of 1-OH-acetone and 1 mL of $NH_4OH$. When a higher volume of $NH_4OH$ is used in the reaction, the yield of the reaction drops by more than 10%.

In summary, reaction conditions (temperature, time, C:N ratio, and pH) are optimized to maximize quantity of pyrazines. Results demonstrated that at optimized conditions (C:N=1:2, temperature=120° C., reaction time=16 hours, and pH=11-12) at least 19-20 different pyrazines are synthesized using hydroxyacetone as the sole carbon source. The absence of any detectable amounts of the molecules pyrazine and/or methylpyrazine from the synthesized pyrazines supports the discovery that the carbon source (i.e., the $\alpha,\beta$-hydroxyketone) influences the structures of the pyrazines produced from reaction of the carbon source with a nitrogen source.

Example 3

The effects of amino acids and aldehyde additions into a separate reaction of 1-OH-acetone and $NH_4OH$, according to the parameters of Example 2 above, with C:N ratio of 1:2 mixed with 10 mL $H_2O$ at 120° C. for 12 hours are measured.

Two different amino acids are tested as an additional source of nitrogen. In each reaction, 0.2 grams of amino acid are added separately to each reaction so that it is possible to study how the additional amino acids affect the pyrazine synthesis and its yield. In a separate reaction, isovaleraldehyde is added to the optimized reaction to study the effect on pyrazine synthesis and yield. When the hydrolyzed F1 protein is used as a source of additional nitrogen, 10 mL of hydrolyzed F1 proteins (which contain approximately 0.2 gram of different amino acids) was used. In this reaction, $H_2O$ is not added since the hydrolyzed F1 proteins are contained within the 10 mL of $H_2O$.

It is observed that when isoleucine is used as a possible additional source of nitrogen, the concentrations of 2,5-dimethyl-3-(2-methylbutyl) pyrazine and 2,5-dimethyl-3-(3-methylbutyl) pyrazine increase. In a separate reaction, when threonine is used as an additional source of nitrogen, the concentrations of 2,5-dimethyl-3-(2-methylbutyl) pyrazine and 2,5-dimethyl-3-(3-methylbutyl) pyrazine increase and the 2,6-dimethyl-3-(2-methylbutyl) pyrazine yield increases. It is interesting to note that the total yields of pyrazines are similar when threonine or isoleucine is added to the reaction. Both compounds increase the total yield of pyrazines by more than 7%.

The addition of isovaleraldehyde to a separate reaction of 1-OH-acetone and $NH_4OH$ causes the percent yield of 2,5-dimethyl-3-(2-methylbutyl) pyrazine and 2,5-dimethyl-3-(3-methylbutyl) pyrazine to increase from 0 to 14 and 13 mg, respectively. The total yield of pyrazines increases by more than 20 percent.

Instead of a pure amino acid, a mixture of amino acids prepared from the hydrolysis of F1 proteins is used in the reaction. Since hydrolyzed F1 proteins are already in an aqueous solution, no water is added to the mixture. For this purpose, 10 mL of hydrolyzed F1 proteins which contained about 0.2 g of amino acid and 10 mL of $H_2O$ is reacted with -1-OH-acetone and $NH_4OH$ with a C:N ratio of 1:2 at 120° C. for 16 hours. The yield of 2,5-dimethylpyrazine increases by more than 80% and the yield of 2,5-dimethyl-3-(2-methylbutyl) pyrazine and 2,5-dimethyl-3-(3-methylbutyl) pyrazine increases from 0 to more than 1 mg. Without being limited by theory, the alkyl portion of the amino acid is converted to a Strecker aldehyde which reacts with the ammonium hydroxide to form an imine which in turn is incorporated into a pyrazine structure.

The effects of different temperatures and C:N ratios (1:1 and 1:2) on the synthesis of pyrazines using 1-OH-acetone and $NH_4OH$ in the presence of additional amino acids/aldehyde is tested. In these studies, increasing the temperature from 100 to 120° C. and C:N ratio, increases the yield of pyrazines.

In summary, addition of amino acids, selected aldehydes, or hydrolyzed F1 protein increases not only percent yield of certain pyrazines, but also increases the number of synthesized pyrazines.

Example 4

Pyrazines are synthesized according to Examples 2 and 3 above, except 1-OH-2-butanone is used as a carbon source instead of 1-OH-acetone.

For this purpose, 1 gram of 1-OH-2-butanone is reacted with 1 mL of $NH_4OH$ and 10 mL of $H_2O$ at 120° C. for 16 hours. No methyl pyrazines are formed. All pyrazines formed contain ethyl or higher branched alkanes. The yield of pyrazines is, however, not as high as when 1-OH-acetone is used. The pyrazines synthesized from a reaction using 1-OH-2-butanone and $NH_4OH$ with C:N of 1:2 at 120° C. for 16 hours includes 2,6-diethylpyrazine; 2,5-diethylpyrazine; 2-ethyl-3,5,6-trimethylpyrazine; 3,5-dimethyl-2(n-propyl)pyrazine; 3,6-dimethyl-2-(n-propyl)pyrazine; 2,5-diethyl-3-methylpyrazine; 2,3-diethyl-5,6-dimethylpryazine; trans-3-methyl-2-(n-propyl)-6-(butenyl)pyrazine; 2,5-dimethyl-3-ethylpyrazine.

As mentioned earlier, with 1-OH-acetone as the carbon source, the molecules pyrazine and methylpyrazine are not produced. With 1-OH-2-butanone, the molecules pyrazine, methylpyrazine, and dimethylpyrazine are not produced, confirming that the carbon source is overwhelmingly dictating the structure of the pyrazines. Results further show that by changing the carbon source from 1-OH-acetone to 1-OH-2-butanone, one can control the type of pyrazines being synthesized.

Example 5

The reaction of 1-OH-acetone and $NH_4OH$ according to Example 2 above is accomplished on a larger scale using a larger Parr reactor with greater reaction volume.

100 grams of 1-OH-acetone is reacted with 100 mL of $NH_4OH$ and 1000 mL of $H_2O$ at 120° C. for 16 hours in a 1.5 liter Parr high pressure vessel. After the reaction is complete, the mixture is cooled and transferred into a glass bottle.

It is noted that in the bottom of the vessel is a considerable amount of a tar like material which is only soluble in MeOH. The addition of $H_2O$ to the top of this material causes it to become hard. It is discovered that concentration can play a significant role in the presence or absence of the tar like material. For all optimization studies, the amount of tar at the bottom of reaction vessel is low. For this reason, a small volume of methanol (1 mL) is sufficient to dissolve everything and include it with the remaining reaction material. For large reactions, the mass of tar is higher and at least 100-200 mL of methanol is required to dissolve it.

After the completion of the reaction, the aqueous solution is distilled (3×375 mL) at 130-140° C. In each distillation (375 mL), approximately 175 mL of aqueous solution containing different pyrazines is collected (light yellow color— total volume about 500 mL). Next, the distilled materials (3×175 mL) are combined and passed through a $C_{18}$ column (15×2.5 cm packed with SPE material) in order to remove the pyrazines from the water. After removal of the water from the $C_{18}$ column, trapped pyrazines are eluted using ethanol. Next, ethanol is removed using a rotary evaporation and vacuum. Due to the presence of some water in the final product, pyrazines are extracted into MTBE and dried over sodium sulfate. Next, MTBE is removed using a rotary evaporator and vacuum. A vial with the solution 1 label contains most of the pyrazines after MTBE is removed.

It is important to note here that three pyrazines are not distilled and remain in the reaction product due to their higher boiling points. This contributed to a lower percent yield. These pyrazines are identified as 2-(2-methylpropyl) 3,5-dimethylpyrazine (12.57 min), 2,6-dimethyl-3-isobutylpyrazine (12.74 min), and 2(2-methylpropyl) 3,5,6-trimethylpyrazine (12.95 min).

Figure 3:
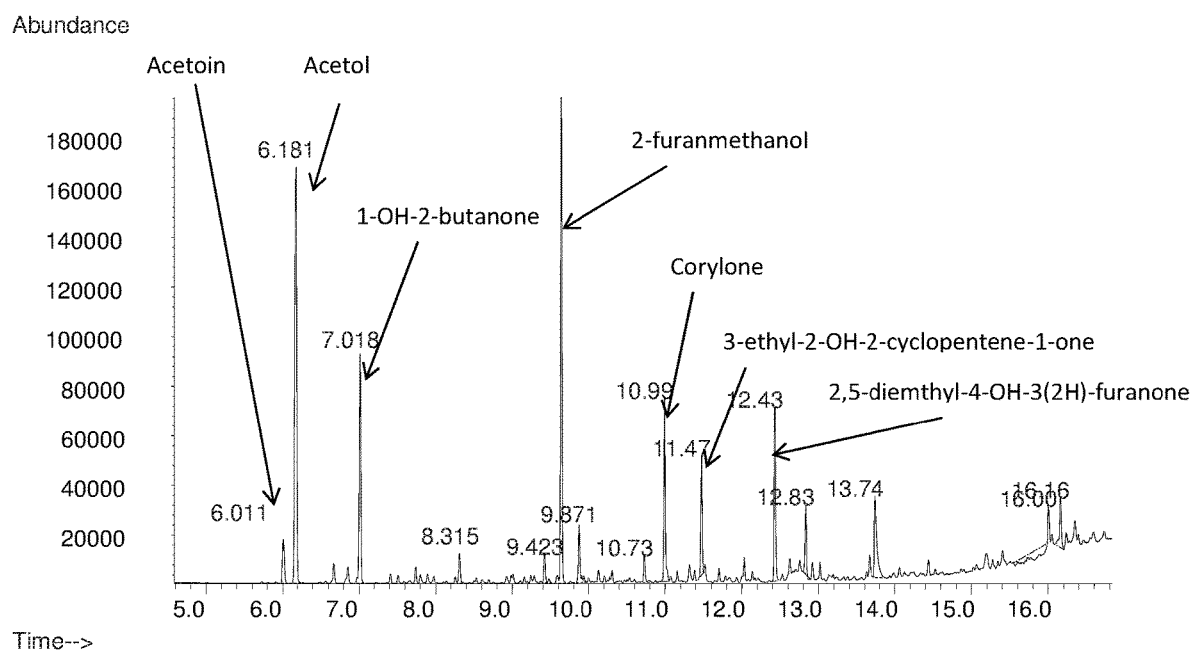
FIG. 3 shows the GC/MS analysis of glucose reacted with a phosphate buffer at 140° C. for 60 min and extracted with dichloromethane (DCM)

DCM (200-250 mL) is used to extract the remaining three pyrazines from the reaction solution after distillation. Next, DCM is removed from the solution using a rotary evaporator and vacuum while the thick dark solution is later transferred to the second vial and labeled as solution 2. FIG. 3 shows a chromatogram of this sample.

The yield of total pyrazines from distillation of 1200 mL of reaction solution (100 grams of 1-OH-acetone+100 mL of $NH_4OH$) is about 60% compared to the 12 mL reaction (1 gram of 1-OH-acetone+1 mL of $NH_4OH$). This yield does not include the three pyrazines that remained in the post distillation reaction mixture.

Solution 1 from above is used for the gas chromatography olfactometry (GCO) evaluations. The pyrazine sample is analyzed using an Agilent 7890A Series GC with 5975C MSD and ODP3 equipped with a Gerstel Multipurpose Sampler with SPME capability. The instrument method is developed for the sample to obtain better separation of the pyrazines and suitable analyzing duration for the olfactory analysts. The transfer line in ODP3 is heated to 260° C. The sample is prepared by pipetting two drops of the sample into a 20 mL SPME screw cap vial. An empty vial is analyzed before and after the sample. The gas chromatographic column separated the pyrazines and they were detected/evaluated by humans using a subjective smell test as they exited the column. The pyrazines identified include: methylpyrazine; 2,6-dimethylpyrazine; 2,5-dimethylpyrazine; 2-ethyl-5-methylpyrazine; 2-ethyl-6-methylpyrazine; trimethylpyrazine; 2,5-dimethyl-3-propylpyrazine; 3-ethyl-2,5-dimethylpyrazine; 2,5-dimethyl-3-isopropylpyrazine; 2-ethyl-3,5-dimethylpyrazine; tetramethylpyrazine; 2-methyl-5-propylpyrazine; 2,3,5-trimethyl-6-propylpyrazine isomer 1; 2,3-diethyl-5-methylpyrazine; 2,3,5-trimethyl-6-ethylpyrazine; 3,5-dimethyl-2-propylpyrazine; 2,3,5-trimethyl-6-propylpyrazine isomer 2; 2,3,5-trimethyl-6-propylpyrazine isomer 3; trimethyl-1-propenylpyrazine (Z)-isomer 1; 5H-clyclopentapyrazine, 6,7-dihydro-2,5-dimethyl pyrazine isomer 1; 5H-clyclopentapyrazine, 6,7-dihydro-2,5-dimethyl pyrazine isomer 2; trimethyl-1-propenylpyrazine (Z)-isomer 2; 2,3-dimethyl-3-(1-propenyl)pyrazine (Z) isomer 1; trimethyl-1-propenylpyrazine (Z)-isomer 3; 2,3-dimethyl-3-(1-propenyl)pyrazine (Z); 2-isopropenyl-3,6-dimethylpyrazine; trimethyl-1-propenylpyrazine (Z)-isomer 4; trimethyl-1-propenylpyrazine (Z)-isomer 5; trimethyl-1-propenylpyrazine (Z)-isomer 6; trimethyl-1-propenylpyrazine (E)-isomer 1; trimethyl-2-propenylpyrazine; trimethyl-1-propenylpyrazine (E)-isomer 2. It is noted that the methylpyrazine compound, although present, was present in a lower amount than typical for traditional sugar carbon source reactions.

Four flavor analysts evaluate the individual olfactory characters from the ODP portal in four separate sessions. The individual pyrazines, based on the four independent assessments, are very positive. Expected descriptors for the aroma of substituted pyrazines are found. Nutty, roasted, toasted, chocolate, peanut, musty, brown and complex are frequent descriptors. These are all positive flavor characteristics.

Example 6

Alpha hydroxy ketones (acetol) are produced from sugar to ultimately be used as the carbon source in sugar ammonia reactions. Sodium hydroxide is used as a base to optimize different parameters such as sugar type, temperature, reaction time, pH, and base concentration in order to maximize the yield of acetol.

Glucose, Fructose, 1-OH-acetone (acetol), 1-OH-2-butanone (acetoin), sodium hydroxide, sodium chloride, sodium sulfate anhydrous, hydrochloric acid, methanol, and dichloromethane are obtained from Sigma-Aldrich (St. Louis, Mo.). Synthesis reactions are performed in a 40 mL Parr vessel or an open round bottle flask. For all reactions in which pH is controlled, reactions are performed in round bottom flasks under reflux at 100° C. In each reaction, 0.25, 0.5, or 1.0 gram of a different sugar (glucose, fructose or mixture of both) is mixed with 25 mL of 0.025, 0.05, 0.1 and 0.2 M NaOH. Each reaction is stirred and heated at different temperatures (90-140° C.) for a period of 1-12 hours. The initial pH levels for most of the reactions are approximately 12 and no adjustments are made during the reaction. However, for the reactions in which the pH level is adjusted to 9, hydrochloric acid is used. For reactions in which the pH is kept constant at 12 during the process, 10-40 µL of 10 M NaOH is used. After the completion of each reaction, the mixture is cooled and the pH is adjusted to 6.0-6.5 using 1 M HCl. Next, 1 mg of acetoin is added to the reaction mixture as an internal standard. The mixture is extracted 4 times with 8-10 mL of dichloromethane. All four extraction solvents are combined and dried with sodium sulfate.

All GC/MS analyses are performed using the same equipment and operating parameters as those used in Example 1 above. MS Wiley library is used to identify peaks. For quantitative analysis, the calibration curve is prepared using a concentration of acetol and a response factor ratio of acetol/acetoin. It is important to note here that acetoin is not detected in any reactions performed at 90, 100 and 120° C. However, acetoin residue is found in the reaction where the temperature is set to 140° C. For this purpose, acetoin concentrations are determined in the reaction and this value is accounted for in all calculations.

GC/FID is used to prepare the calibration curve for the quantification of acetol in all reactions. Next, the following parameters are varied to determine the optimum conditions for the synthesis of acetol.

First, two different type of sugars (glucose, fructose, and a mixture of both) are used to determine which sugar provides a higher yield of acetol. In each reaction, 0.5 grams of sugar is mixed with 25 mL of 0.05M NaOH. Each reaction is heated for 60 minutes at 100° C. Table 1 below shows the reaction conditions and the corresponding mg of acetol that were obtained from each reaction. It can be observed that glucose generated a high mass of acetol when it was used in the reaction.

TABLE 1

Effect of sugar type on synthesis of acetol

| Sugar | Wt. gr | pH | NaOH | Temp, °C. | Time, min | mg acetol* | % Yield wt. base-mole base |
|---|---|---|---|---|---|---|---|
| Glucose (Glu) | 0.5 | 12-7.5 | 0.05M | 100 | 60 | 3.77 | 0.75-1.8 |
| Fructose (Fru) | 0.5 | 12-7.5 | 0.05M | 100 | 60 | 2.97 | 0.59-1.4 |
| Glu + Fru | 0.25 + 0.25 | 12-7.5 | 0.05M | 100 | 60 | 3.18 | 0.64-1.5 |

*% RSD varied from 2-5

In this part of study, since it is required to adjust the pH during the reaction process, all reactions are performed under reflux in an open round flask instead of in a closed Parr reactor. Three different experiments are performed. In the first experiment, the pH is measured every 10 minutes and no adjustment is made to the pH. In the second experiment, the pH is measured every 10 minutes and, if it is required, the pH is adjusted to the initial value (12.0) using 10M NaOH. In the third experiment, initial pH is adjusted to 9.0 and then the reaction is started, with pH measurements taking place every 10 minutes (without adjustments).

Results from the pH measurements show that the pH drops from 12.0 to around 9 within the first 10 minutes of the reaction at 100° C. At the end of 30 minutes, the pH of the reaction is approximately around 7-8 and remains constant during the remaining reaction time. For the experiments where the pH is maintained around 12.0, it becomes necessary to add approximately 15-20 µL of 10M NaOH to the reaction every 10 minutes. After 40 minutes, the pH remains constant around 11-12.

Table 2 below shows reaction conditions and the mg of acetol obtained from each reaction using different pH conditions. When the pH is kept constant around 12, the highest mass of acetol is obtained.

TABLE 2

Effect of pH on synthesis of acetol

| Sugar | Wt. gr | pH | NaOH | Temp, °C. | Time, min | mg acetol* | % Yield wt. base-mole base |
|---|---|---|---|---|---|---|---|
| Glu | 0.5 | 12-7.5 | 0.05M | 100 | 60 | 2.79 | 0.56-1.4 |
| Glu | 0.5 | 12.0-12.0 | 0.05M | 100 | 60 | 4.94 | 0.99-2.4 |
| Glu | 0.5 | 9-7.5 | 0.05M | 100 | 60 | 0.00 | 0.00-0.0 |

*% RSD varied from 5-9

Three different sugar concentrations are tested in order to determine how sugar concentration effects acetol production. Therefore, reactions are performed using 0.25, 0.5 and 1 gram of glucose in 25 mL of 0.05M NaOH solution. Each reaction is heated at 100° C. for 60 minutes using a Parr reactor. Table 3 below shows the results of this study. It is observed that when 0.25 gram of glucose is used in a reaction, the highest amount of acetol is obtained.

Without being limited by theory, it is believed that when sugar concentration is high, acid formation during the reaction process minimizes the production of acetol. When the sugar concentration is less, acid formation will take longer while the pH is high enough to cause the formation of acetol.

TABLE 3

Effect of Sugar Concentration on synthesis of acetol

| Sugar | Wt. gr | pH | NaOH | Temp, °C. | Time, min | mg acetol* | % Yield wt. base-mole base |
|---|---|---|---|---|---|---|---|
| Glu | 0.25 | 12-7.5 | 0.05M | 100 | 60 | 3.88 | 1.55-3.8 |
| Glu | 0.5 | 12-7.5 | 0.05M | 100 | 60 | 3.77 | 0.75-1.8 |
| Glu | 1 | 12-7.5 | 0.05M | 100 | 60 | 2.77 | 0.28-0.7 |

*% RSD varied from 5-7

Four different concentrations of NaOH (0.2, 0.1, 0.05 and 0.025M) are used for the preparation of acetol. Table 4 below shows results of this study. As can be observed, when the NaOH concentration is 0.025M, the least amount of acetol is obtained. However, as the concentration increases from 0.025 to 0.1M, the mass of synthesized acetol increases too. When the concentration of base increases to 0.2M, the amount of acetol decreases. It is noted that the reaction solution smells of burnt sugar compared to the other reactions where the base concentration is lower.

TABLE 4

Effect of NaOH Concentration on synthesis of acetol

| Sugar | Wt. gr | pH | NaOH | Temp, C. | Time, min | mg acetol* | % Yield wt. base-mole base |
|---|---|---|---|---|---|---|---|
| Glu | 0.5 | 12-11.5 | 0.2M | 100 | 60 | 3.35 | 0.67-1.6 |
| Glu | 0.5 | 12-8.5 | 0.1M | 100 | 60 | 5.38 | 1.08-2.6 |
| Glu | 0.5 | 12-7.5 | 0.05M | 100 | 60 | 3.77 | 0.75-1.8 |
| Glu | 0.5 | 12-6.5 | 0.025M | 100 | 60 | 2.01 | 0.40-1.0 |

*% RSD varied from 5-20 (% RSD was 20 for 0.2M NaOH reactions)

The effects of temperature on the synthesis of acetol using NaOH and glucose are investigated. For this purpose, different temperatures ranging from 90 to 140° C. are studied. Results for reaction temperatures of 90, 100 and 120° C. are similar while the reaction at 140° C. yields approximately 25% more acetol than the other reactions with lower temperatures. Table 5 below shows results of this study.

TABLE 5

Effect of Reaction Temperature on synthesis of acetol

| Sugar | Wt. gr | pH | NaOH | Temp, ° C. | Time, min | mg acetol* | % Yield wt. base-mole base |
|---|---|---|---|---|---|---|---|
| Glu | 0.5 | 12-7.0 | 0.05M | 90 | 60 | 3.37 | 0.67-1.6 |
| Glu | 0.5 | 12-7.5 | 0.05M | 100 | 60 | 3.77 | 0.75-1.8 |
| Glu | 0.5 | 12-7.5 | 0.05M | 120 | 60 | 3.23 | 0.65-1.6 |
| Glu | 0.5 | 12-6.8 | 0.05M | 140 | 60 | 4.58 | 0.92-2.2 |

*% RSD varied from 2-8

The effects of reaction time on the synthesis of acetol is also studied. Reactions are performed using identical conditions while reaction times are varied from 60 to 720 minutes. Table 6 below shows the results of this study. The results show that with increasing reaction times, there is no significant change in the yield of acetol.

TABLE 6

Effect of Reaction Time on synthesis of acetol

| Sugar | Wt. gr | pH | NaOH | Temp, ° C. | Time, min | mg acetol* | % Yield wt. base-mole base |
|---|---|---|---|---|---|---|---|
| Glu | 0.5 | 12-7.5 | 0.05M | 100 | 60 | 3.77 | 0.75-1.8 |
| Glu | 0.5 | 12-6.8 | 0.05M | 100 | 120 | 3.24 | 0.65-1.6 |
| Glu | 0.5 | 12-6.8 | 0.05M | 100 | 240 | 3.72 | 0.74-1.8 |
| Glu | 0.5 | 12-6.9 | 0.05M | 100 | 720 | 3.38 | 0.68-1.6 |

*% RSD varied from 2-6

In the last part of this study, based on results obtained from previous reactions, different reactions are performed using optimized conditions. In reaction A, 1 gram of glucose is reacted with 0.05M NaOH under reflux at 100° C., while the pH is kept constant around 11-12. This reaction continues for 120 minutes until the pH remains constant and does not change. The yield of acetol is 6.7 mg. In reaction B, a Parr vessel is used at 100° C. to react 0.5 gram of HFTS with 25 mL of 0.05M NaOH for 60 minutes. The acetol yield is 3.42 mg. When the same reaction is performed under optimized conditions, (0.1M NaOH and 140° C. for 60 min) the acetol yield increases by 100% to 6.69 mg (Rxn D). Similar results are obtained when optimized conditions are applied to 0.5 grams of glucose (Rxn C). The acetol yield increases to 8.2 mg. Using identical reaction conditions, but using 50% less glucose (0.25 gram), the yield of acetol decreases to 5.32 mg.

TABLE 7

Effect of Different Reaction Conditions on synthesis of acetol

| | | Sugar | Wt. gr | pH | NaOH | Temp, ° C. | Time, min | mg acetol | % Yield wt. base-mole base |
|---|---|---|---|---|---|---|---|---|---|
| Rxn A | Reflux | Glu | 1 | 12.0-11.0+ | 0.05M | 100 | 120 | 6.70 | 0.67-1.6 |
| Rxn B | Parr | HFTS* | 0.5 | 12.0-7.5 | 0.05M | 100 | 60 | 3.42 | 0.68-1.7 |
| Rxn C | Parr | Glu | 0.5 | 12.5-6.5 | 0.1M | 140 | 60 | 8.20 | 1.64-4.0 |
| Rxn D | Parr | HFTS | 0.5 | 12.5-6.7 | 0.1M | 140 | 60 | 6.69 | 1.34-3.3 |
| Rxn E | Parr | Glu | 0.25 | 12.0-8.5 | 0.1M | 140 | 60 | 5.32 | 2.13-5.2 |

*"HFTS" stands for high fructose tobacco syrup
+pH was kept constant around 12

In summary, different parameters such as sugar type, reaction temperature, reaction time, pH, base and sugar concentrations are optimized for the synthesis of acetol from reaction sugars and sodium hydroxide. It is demonstrated that the highest yield of acetol can be obtained when the reaction is performed at 140° C. using 0.1M sodium hydroxide and 0.5 grams of glucose for 60 minutes. It is noticed that the pH of the reaction can be changed rapidly (within 10 minutes) from 12 to 6.5 if the base concentration is low or the sugar concentration is high. Also, it is noted that at high temperatures (140° C.), the reaction product contains small amounts of acetoin (along with the acetol). It is important to note that hydroxy ketones (acetoin) have been prepared from glucose using biotechnical approaches with yield greater than 90%. However, published chemical conversions of glucose to hydroxy ketones are much less at ~9%.

Example 7

Pyrazines are produced using glucose as a carbon source.
As illustrated in Example 6 above, acetol can be synthesized via a reaction of 0.1 N NaOH and glucose using optimum conditions (0.5 gram glucose reacted with 25 mL of 0.1 N NaOH at 140° C. for 60 min). The yield of acetol was approximately 2% based on the glucose weight.

A publication by Nodzu (R. Nodzu, On the action of phosphate upon hexoses, The formation of acetol from glucose in acidic solution of potassium phosphate. Bull Chem. Soc. Japan, 10, 122-130, 1935, which is herein incorporated by reference) demonstrated that acetol with 4% yield (based on the weight of the glucose) can by synthesized from a reaction of a 40% phosphate buffer solution with a pH of 6.5-6.8 with glucose at a temperature of 100-120° C. They demonstrated that a higher yield of acetol can be obtained at a pH of 7.0-7.1 and as pH decreased, the yield of acetol decreased.

This Example first illustrates the preparation of acetol via a reaction of 0.1 N NaOH and glucose under optimized conditions. A method to isolate the acetol from the reaction mixture is then illustrated. Finally, it is demonstrated that the above mixture, without the isolation of acetol acetoin, can be reacted with $NH_4OH$ to synthesize different branched pyrazines.

Glucose, 1-OH-acetone (acetol), 1-OH-2-butanone (acetoin), sodium hydroxide, di-sodium hydrogen phosphate/sodium hydroxide buffer solution pH=12, potassium phosphate dibasic, potassium phosphate monobasic, sodium chloride, sodium sulfate anhydrous, hydrochloric acid, methanol, and dichloromethane are obtained from Sigma-Aldrich (St. Louis, Mo.).

Synthesis of acetol is performed in a 40 mL or 1.5 L Parr vessel. To synthesize acetol, 0.5 grams of glucose is mixed for every 25 mL of 0.1 N NaOH or buffer solution. Each reaction is stirred and heated at 140° C. for a period of 60 min. The initial pH levels for all reactions are approximately 12 and no adjustments are made during the reaction. After the completion of each reaction, the mixture is cooled and the quantity of both acetol and sugar are measured using GC and HPLC. For acetol quantification, 25 mL of solution is spiked with 1 mg of acetoin as an internal standard and extracted with 30-35 mL of DCM. Next, the extracted DCM solution is dried over sodium sulfate and analyzed via GC/FID for quantification.

The synthesis of pyrazines is performed in the same Parr vessel. Reactions are performed by reacting the acetol synthesized from the reaction of sugar and 0.1 N NaOH. In this reaction, every 25 mL of solution is reacted either with 0.25, 0.5 or 1 mL of $NH_4OH$. Reactions are obtained at 120 or 140° C. for a period of 17 hours. Next, each reaction mixture is cooled and the pyrazines are extracted and quantified. In each extraction 0.25 mg of $d_6$-2 methyl pyrazine is added as an internal standard and the solution is extracted with 30-35 mL of DCM as a solvent. Next, the DCM solution is dried over sodium sulfate and analyzed via GC/MS for quantification. Extracted ions are used to quantify each pyrazine.

All GC/MS analyses are performed using the same equipment and operating parameters as those used in Example 1 above. MS Wiley library is used to identify each pyrazine. For quantitative analysis, the calibration curve is prepared using a concentration of acetol and a response factor ratio of acetol/acetoin. It is noted here that acetoin was not detected in any reactions performed at 90, 100 and 120° C. However, acetoin residue is found in the reaction where the temperature is set to 140° C. Therefore, acetoin concentrations are determined in the reaction and this value is accounted for in all calculations.

All HPLC/RI separations are performed using Sugar-Pak (300×6.5 mm) columns from Waters (Milford, Mass.). An Agilent 1100 series HPLC equipped with a quaternary pump, refractive index (RI) detectors, auto-sampler, and oven heater set to 80° C. is employed. The isocratic mobile phase for analysis of sugar is 0.005% EDTA disodium dihydrate. The flow rate is set at 0.5 mL/min for these analyses.

First, acetol is synthesized using a buffer solution. Due to rapid changes in the pH of a solution in a reaction of glucose with 0.1 N NaOH solution for synthesis of acetol, a buffer solution with a pH of 12 (purchased from Sigma Aldrich) is used in the synthesis of acetol instead of a 0.1 N NaOH solution. In this study, 25 mL of di-sodium hydrogen phosphate/sodium hydroxide buffer solution pH=12 is reacted with 0.25 or 0.5 gram of glucose at 140° C. for 60 minutes. Results show that the concentration of acetol in the reaction product is much higher (2×) when a buffer solution is used to perform the synthesis. Table 8 below shows the results of this study.

TABLE 8

Effect of glucose concentration on preparation of acetol using basic buffer solution from Sigma Aldrich

| Solution | Glucose mg | Buffer Volume mL | pH | Rxn, Time Min | Temp., ° C. | Acetol, mass mg | % Yield based on Glucose |
|---|---|---|---|---|---|---|---|
| Buffer | 0.25 | 25 | 12 | 60 | 140 | 6.53 | 5.2 |
| Buffer | 0.50 | 25 | 12 | 60 | 140 | 15.3 | 6.1 |

When a similar buffer is prepared (mixing 7.1 gram of $Na_2HPO_4$ and 1 gram of NaOH in 100 mL of $H_2O$ with a pH of approximately 12 and capacity of 0.05 N) and reacted with glucose at 140° C. for 60 minutes, the reaction mixture did not show a presence of acetol. This reaction is repeated three times and acetol is not found in any of the reaction products. However, when a similar buffer with the same pH but lower capacity (0.025 N) is used, acetol is found in the reaction product and concentration of it is much higher than when 0.1 N NaOH was used. As such, it is determined that the buffer type, capacity, pH, and reaction temperature have an effect on the synthesis of acetol using glucose.

Next, the acetol concentration in a reaction of glucose with 40% phosphate buffer with pH 6.5-7.0 is determined. 25 mL of a 40% potassium phosphate buffer pH=6.5-6.8 is reacted with 0.5 or 1 gram of glucose at 140° C. for 60 minutes using a Parr reactor. Table 9 below shows the mass of acetol obtained from a reaction of a 40% phosphate buffer (25 mL) at a pH of 6.5-6.8 with different concentrations of glucose. It is noted here other types of hydroxy ketones such as 3-OH-2-butanone and 1-OH-2-butanone are also formed in this reaction. The quantity of these hydroxy ketones is not measured. FIG. 3 shows the GC/MS analysis of glucose reacted with a phosphate buffer at 140° C. for 60 min and extracted with DCM.

TABLE 9

Mass of Acetol obtained from reaction of 40% phosphate buffer with different concentration of glucose

| Solution | Glucose (g) | Volume (mL) | Rxn, Time (min) | Temp. (° C.) | Acetol, mass (mg) | % Yield based on Glucose |
|---|---|---|---|---|---|---|
| Buff. Phosph. | 0.5 | 25 | 60 | 140 | 23.57 | 4.7 |
| Buff. Phosph. | 0.5 | 25 | 60 | 140 | 16.4 | 3.3 |
| Buff. Phosph. | 0.5 | 25 | 60 | 140 | 15.92 | 3.2 |
| Buff. Phosph. | 1 | 25 | 60 | 140 | 44.3 | 4.4 |
| Buff. Phosph. | 1 | 25 | 60 | 140 | 44.4 | 4.4 |

Next, the glucose and acetol concentrations in 300 mL and 1 L reactions are determined. 6 grams of glucose is reacted with 300 mL of 0.1 N NaOH for 60 min at 140° C. After the reaction is cooled, both acetol and glucose concentrations in the solution are obtained. A small amount (0.964 mg/mL) of glucose is detected in the reactant. This corresponds to about less than 5% of the glucose that remained unreacted. Table 10 below shows the concentration of acetol in this reaction. It can be determined that the concentration of acetol is about 12 mg for every 25 mL. Two additional reactions are performed using 1 liter of 0.1 N NaOH and 20 grams of glucose using a high pressure reaction vessel. Both reactions are performed at 130-140° C. for 60 minutes. Both glucose and acetol concentrations are determined. In both 1 liter reactions, concentrations of glucose are less than 1 mg/mL (0.945 and 0.958 mg/mL). Table 10 below also shows the concentration of acetol in each 1 liter reaction. Again, the acetol concentration is about 12 mg for every 25 mL.

TABLE 10

Calculated mass of Acetol from reaction of 0.1N NaOH with different mass of glucose

| Solution | Glucose (g) | Volume (mL) | Rxn, Time (min) | Temp. (° C.) | Acetol, mass (mg) | % Yield based on Glucose |
|---|---|---|---|---|---|---|
| 0.1N NaOH | 6 | 300 | 60 | 140 | 140.26 | 2.3 |
| 0.1N NaOH | 6 | 300 | 60 | 140 | 140.68 | 2.3 |
| 0.1N NaOH | 20 | 1000 | 60 | 140 | 490.12 | 2.5 |
| 0.1N NaOH | 20 | 1000 | 60 | 140 | 470.08 | 2.4 |

Next, acetol is isolated from the reaction of glucose with 0.1N NaOH. Different methods are used to isolate acetol from the reaction of 0.1 N NaOH and glucose. Previous results for the isolation of pyrazines via distillation demonstrated that pyrazines with a boiling point of 140° C. were isolated from the reaction mixture. Therefore, a distillation apparatus set at 120-140° C. is used to isolate acetol from the reaction mixture. For this purpose, 100 mL of a reaction mixture of 0.1 N NaOH and glucose is distilled at 140° C. After the collection of 40 mL of distillation solution, both the distilled and the remaining materials are extracted with DCM. GC/FID analysis shows that only 15-20% of acetol is distilled while more than 80-85% of acetol remains in the reaction mixture.

Similar results are obtained when a reaction mixture of glucose with a 40% phosphate buffer at 140° C. for 60 minutes is distilled. For this distillation, water is continuously added to the flask during the distillation to keep the distilled solution volume constant. After the collection of about 10 mL solution via distillation, approximately 10 mL $H_2O$ is added to the distillation flask to compensate for the volume lost. A total of 4×10 mL fractions are collected. Acetol is observed in each fraction. Analysis of the remaining reaction mixture with DCM shows a presence of more acetol in the solution. The isolation of acetol can be obtained if this distillation continues for several hours.

In a second method, column chromatography is used to isolate the acetol from the reaction mixture. For this purpose a 30×2.0 cm glass (or metal) column (packed up to only 12-15 cm) with $C_{18}$ (particulate size of 40-60 μm and 90 Å pore size) is used to isolate the acetol. After washing the column with methanol followed by a 0.1% FA solution, 25 mL of the reaction mixture containing acetol is passed through the column. All of the solution is collected during this isolation. After pushing the solution through the column (fraction 1, 25 mL), 25 mL of deionized $H_2O$ is used to wash the material from the column (Fraction 2). Next, the column is washed with an additional 25 mL $H_2O$ until clean $H_2O$ is eluted from the column (Fraction 3). Then the column is dried with $N_2$, and the remaining analytes trapped in the column are eluted with 100% MeOH (Fraction 4). All fractions are extracted with DCM and analyzed via GC/FID. Results showed that most of the acetol is eluted with fractions 1 and 2 while fractions 3 and 4 did not contain any acetol. It is noted here that after passing the reaction mixture through the $C_{18}$ packing, it is very difficult to use the packing for another reaction mixture cleanup. It is very difficult to clean up the packing. In summary, isolating the hydroxy ketones from the reaction product can be timely and expensive.

Next, pyrazines are synthesized from the reaction product of glucose and sodium hydroxide with $NH_4OH$, without first isolating the hydroxy ketones. After the preparation of acetol via reacting 0.5 grams glucose with 25 mL of 0.1 N NaOH at 140° C. for 60 minutes, it is determined that the reaction mixture contained about 10-12 mg of acetol/25 mL of solution. For this purpose, 25 mL of the solution is reacted with 0.5 or 1 mL of $NH_4OH$ for a period of 17-18 hours at 120-140° C. to determine the type and the percent yield of the pyrazines. Each reaction is repeated twice. Table 11 below shows list of pyrazines that are detected including their elution time from the GC column. Results are similar when the volume of $NH_4OH$ is changed from 0.5 to 1 mL.

TABLE 11

List of synthesized pyrazines

| Retention time | Peak # | Analyte |
|---|---|---|
| 5.82 | 1 | Internal Standard |
| 5.08 | 2 | Pyrazine |
| 5.82 | 3 | 2-Methylpyrazine |
| 6.48 | 4 | 2,6-Dimethylpyrazine |
| 6.56 | 5 | 2,5-Dimethylpyrazine |
| 6.76 | 6 | 2,3-Dimethylpyrazine |
| 7.178 | 7 | 2-Ethyl-5-Methylpyrazine |

TABLE 11-continued

List of synthesized pyrazines

| Retention time | Peak # | Analyte |
|---|---|---|
| 7.24 | 8 | 2-Ethyl-6-Methylpyrazine |
| 7.4 | 9 | 2,3,5-Trimethylpyrazine |
| 7.95 | 10 | 2,6-Dimethyl-3-Ethylpyrazine |
| 8 | 11 | 2,Ethyl-2,5-Dimethylpyrazine |
| 8.1 | 12 | 2,3,5,6-Tetramethylpyrazine |
| 8.44 | 13 | 3,5-Diethyl-2-Methylpyrazine |
| 8.63 | 14 | 2,5-Dimethyl-3Propylpyrazine |
| 8.81 | 15 | 2,5-Diethyl-3,6-Dimethylpyrazine |
| 9.4 | 16 | 6,7-DiHydrocyclo-5-Methylcyclopentapyrazine |
| 9.669 | 17 | 2-Isoprophenylpyrazine |
| 9.69 | 18 | 2,3-Dimethyl-5-Isopentylpyrazine |
| 9.89 | 19 | 2,5-Dimethyl-3-(3-methylbutyl)pyrazine |
| 9.96 | 20 | 6,7-DiHydrocyclo-2,5-Dimethyl-5H-cyclopentapyrazine |
| 10.238 | 21 | 2-Methyl-5H-6,7-diHydrocyclopentapyrazine |

Similar reactions are performed in the 1 liter scale. Two batches of 1 liter solution are prepared. In each batch, 20 grams of glucose is reacted with 1000 mL of 0.1 N NaOH solution at 140° C. for 60 min. Each solution is cooled and the acetol concentration is measured. Next, in one reaction mixture, 20 mL of NH$_4$OH is added, and in a second reaction mixture, 40 mL of NH$_4$OH is added. Each reaction is heated at 120-130° C. for 17 hours with continuous mixing. After the reactions are cooled, 25 mL of each reaction is spiked with an internal standard (d$_6$-2-methylpyrazine) and extracted with DCM to determine the concentration and distribution of each pyrazine. Each remaining reaction solution is distilled and collected separately. Approximately 125 mL of distilled solution is collected for every 500 mL of reaction mixture. Next, the distilled solution (10 mL) is extracted with DCM and quantified via GC/MS. The total mass of pyrazines is higher than if the solution had not been extracted with DCM, which is due to a higher concentration of pyrazines in the distilled solution. The distribution of pyrazines is almost identical in both extracts. It is noted that both 2-methylpyrazine and pyrazine are detected in large quantities in all reactions when NH$_4$OH is reacted with the reaction mixture of glucose with 0.1 N NaOH. No pyrazines are detected in the extract of the remaining solution after distillation.

Figure 4:
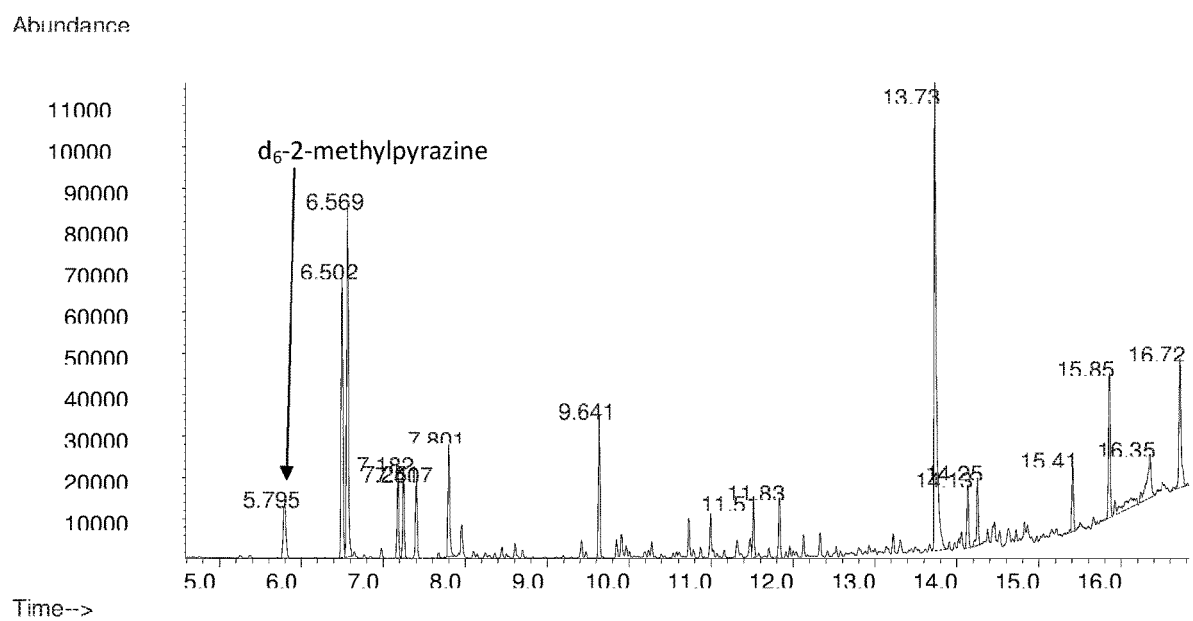
FIG. 4 shows the GC/MS analysis of pyrazines extracted using DCM from a reaction mixture of (1 gram of glucose reacted with 25 mL of 40% phosphate buffer at 140° C. for 60 min) with 1 mL of $NH_4OH$ at 140° C. for 17 hours.
Figure 5:
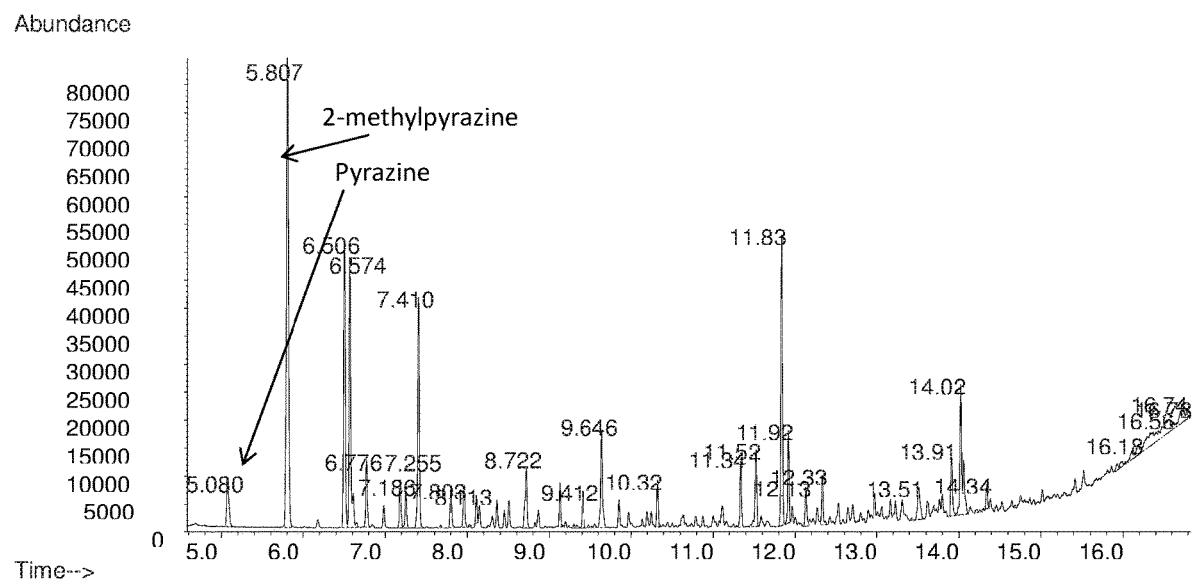
FIG. 5 shows the GC/MS analysis of pyrazines extracted using DCM from 25 mL of a reaction mixture of (0.1 N NaOH reacted with 0.5 gram of glucose at 140° C. for 60 min) reacted with 1 mL of $NH_4OH$ at 140° C.

Next, pyrazines are synthesized from the reaction product of glucose and phosphate buffer with NH$_4$OH, without first isolating the hydroxy ketones. 25 mL of the reaction mixture of a phosphate buffer with pH=6.5-6.8 and glucose (0.5 or 1 gram, solutions A and B, respectively) is reacted with 1 mL of NH$_4$OH at 140° C. for 17 hours. After each reaction is cooled down, 0.25 mg of deuterated 2-methylpyrazine (internal standard) is added to each reaction mixture and the solutions are extracted with DCM. Each extract is analyzed using GC/MS and the mass of pyrazines and their percent distribution is calculated. It is noted that both pyrazine and 2-methylpyrazine are not synthesized in these reactions. Also, the total mass of pyrazines is higher by 20% in solution B when 1 gram of glucose is reacted with a phosphate buffer. Without being limited by theory, it is believed that this is due to a higher concentration of acetol in solution B compared to solution A. FIG. 4 shows the GC/MS analysis of pyrazines extracted using DCM from a reaction mixture of solution B (1 gram of glucose reacted with 25 mL of 40% phosphate buffer at 140° C. for 60 min) with 1 mL of NH$_4$OH at 140° C. for 17 hours. For comparison, FIG. 5 shows the GC/MS analysis of pyrazines extracted using DCM from 25 mL of a reaction mixture of 0.1 N NaOH reacted with 0.5 gram of glucose at 140° C. for 60 min and then reacted with 1 mL of NH4OH at 140° C. In this reaction, both pyrazine and 2-methylpyrazine are detected.

In summary, acetol (and other hydroxy ketones) can be isolated from a reaction mixture of glucose and 0.1 N NaOH using both distillation and column chromatography. Distillation is very time and energy consuming while chromatography can become very expensive. However, it is possible to synthesize pyrazines without the isolation of acetol. When the acetol prepared from the reaction of 0.1 N NaOH and glucose reacted with NH$_4$OH at 140° C. for 17 hours, an array of pyrazines were produced. The pyrazines were isolated via distillation. It is noted that pyrazine and 2-methylpyrazine were synthesized during this process. However, when the acetol prepared from the mixture of glucose and phosphate buffer reacted with NH$_4$OH, similar pyrazines were produced with a similar distribution, but no pyrazine or 2-methyl pyrazine was detected in the reaction mixture.

Many modifications and other embodiments of the invention will come to mind to one skilled in the art to which this invention pertains having the benefit of the teachings presented in the foregoing description. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A method of forming pyrazines comprising:
receiving a reaction solution comprising at least one alpha-hydroxy ketone and at least one nitrogen source;
adding at least one free amino acid to the reaction solution;
heating the reaction solution to a reaction temperature and holding the reaction solution at the reaction temperature for a time sufficient to produce a reaction product comprising at least one substituted pyrazine; and
isolating the at least one substituted pyrazine from the reaction product, wherein the step of isolating the at least one substituted pyrazine from the reaction product comprises at least one of liquid-liquid extraction of the reaction product, liquid-solid extraction of the reaction product, and simple distillation of the reaction product.

2. The method of claim 1, wherein the at least one hydroxy ketone comprises acetol.

3. The method of claim 2, wherein the at least one substituted pyrazine is selected from the group consisting of: 2,3-dimethylpyrazine; 2,6-dimethylpyrazine; 2-ethyl-6-methylpyrazine; 2-ethyl-5-methylpyrazine; trimethylpyrazine; 2,5-dimethyl-3-ethylpyrazine; 2-ethyl-3,5-dimethylypyrazine; tetramethylpyrazine; 2,5-dimethyl-3-propenylpyrazine; 2,3,5-trimethyl-6-isopropylpyrazine; 2-acetyl-4,5-dimethylpyrazine; 3,5-dimethyl-2-methylpropylpyrazine, and combinations thereof.

4. The method of claim 1, wherein the at least one hydroxy ketone comprises acetoin.

5. The method of claim 4, wherein the at least one substituted pyrazine is tetramethylpyrazine.

6. The method of claim 1, wherein the at least one hydroxy ketone comprises 1-hydroxy-2-butanone.

7. The method of claim 6, wherein the at least one substituted pyrazine is selected from the group consisting of: 2,6-diethylpyrazine; 2,5-diethylpyrazine; 2-ethyl-3,5,6-trimethylpyrazine; 3,5-dimethyl-2-(n-propyl)pyrazine; 3,6-dimethyl-2-(n-propyl)pyrazin; 2,5-3-methylpyrazine; 2,3-diethyl-5-methylpyrazine; 2,3-diethyl-5,6-dimethylpryazine; trans-3-methyl-2-(n-propyl)-6-(butenyl)pyrazine; 2,5-dimethyl-3-ethylpyrazine; and combinations thereof.

8. The method of claim 1, wherein the nitrogen source is selected from the group consisting of amino acids, ammonium ions, and combinations thereof.

9. The method of claim 1, further comprising adding at least one aldehyde to the reaction solution.

10. The method of claim 1, wherein the reaction temperature is about 90° C. to about 150° C.

11. A method of forming pyrazines comprising:
receiving a reaction solution comprising at least one alpha-hydroxy ketone and at least one nitrogen source;
adding at least one free amino acid to the reaction solution; and
heating the reaction solution to a reaction temperature and holding the reaction solution at the reaction temperature for a time sufficient to produce a reaction product comprising at least one substituted pyrazine;
wherein the at least one substituted pyrazine is disubstituted, trisubstituted, or tetrasubstituted.

12. The method of claim 1, wherein the at least one substituted pyrazine is disubstituted.

13. The method of claim 1, wherein the at least one substituted pyrazine is trisub stituted.

14. The method of claim 1, wherein at least one substituted pyrazine is tetrasubstituted.

15. The method of claim 1, wherein the at least one substituted pyrazine comprises at least one substituent group having 2 or more carbon atoms.

16. The method of claim 1, wherein the at least one substituted pyrazine comprises at least one substituent group having 3 or more carbon atoms.

17. The method of claim 1, wherein the reaction product is substantially free of the molecule pyrazine and the molecule methylpyrazine.

18. The method of claim 1, further comprising incorporating the at least one substituted pyrazine into a tobacco product.

19. The method of claim 18, wherein the tobacco product is a smoking article or a smokeless tobacco product.

20. A method of forming pyrazines comprising:
receiving a reaction solution comprising at least one alpha-hydroxy ketone and at least one nitrogen source; and
heating the reaction solution to a reaction temperature and holding the reaction solution at the reaction temperature for a time sufficient to produce a reaction product comprising at least one substituted pyrazine;
wherein the at least one substituted pyrazine is disubstituted.

21. The method of claim 1, wherein the at least one free amino acid is selected from the group consisting of serine, alanine, leucine, isoleucine, valine, threonine, phenylalanine, and combinations thereof.

22. A method of forming pyrazines comprising:
receiving a reaction solution comprising at least one alpha-hydroxy ketone and at least one nitrogen source;
adding at least one free amino acid to the reaction solution; and
heating the reaction solution to a reaction temperature and holding the reaction solution at the reaction temperature for a time sufficient to produce a reaction product comprising at least one substituted pyrazine;
wherein the at least one hydroxy ketone comprises acetol; and
wherein the at least one substituted pyrazine is selected from the group consisting of: 2,3-dimethylpyrazine; 2,6-dimethylpyrazine; 2-ethyl-6-methylpyrazine; 2-ethyl-5-methylpyrazine; trimethylpyrazine; 2,5dimethyl-3-ethylpyrazine; 2-ethyl-3,5-dimethylypyrazine; tetramethylpyrazine; 2,5-dimethyl-3-propenylpyrazine; 2,3,5-trimethyl-6-isopropylpyrazine; 2-acetyl-4,5-dimethylpyrazine; 3,5-dimethyl-2-methylpropylpyrazine, and combinations thereof.

23. A method of forming pyrazines comprising:
receiving a reaction solution comprising at least one alpha-hydroxy ketone and at least one nitrogen source;
adding at least one free amino acid to the reaction solution; and
heating the reaction solution to a reaction temperature and holding the reaction solution at the reaction temperature for a time sufficient to produce a reaction product comprising at least one substituted pyrazine;
wherein the at least one hydroxy ketone comprises acetoin.

24. A method of forming pyrazines comprising:
receiving a reaction solution comprising at least one alpha-hydroxy ketone and at least one nitrogen source;
adding at least one free amino acid to the reaction solution; and
heating the reaction solution to a reaction temperature and holding the reaction solution at the reaction temperature for a time sufficient to produce a reaction product comprising at least one substituted pyrazine;
wherein the at least one hydroxy ketone comprises 1-hydroxy-2-butanone.

25. The method of claim 11, wherein the at least one substituted pyrazine is selected from the group consisting of: 2,6-dimethylpyrazine; 2,5-dimethylpyrazine; 2-ethyl-5-methylpyrazine; 2-ethyl-6-methylpyrazine; 2,3,5-trimethylpyrazine; 2-ethyl-3,5-dimethylpyrazine; 2-ethyl-2,5-dimethylpyrazine; 2,3,5,6-tetramethylpyrazine; 2,3,5-trimethyl-6-ethylpyrazine; 2,6-dimethyl-3-propylpyrazine; 2,5-diethyl-3,6-dimethylpyrazine; 2,6-dimethyl-3-(2-methylbutyl)pyrazine; 2,5-dimethyl-3-(2-methylbutyl)pyrazine; 2,5-dimethyl-3-(3-methylbutyl)pyrazine; 2,5-dimethyl-3-propylpyrazine; 2,5-dimethyl-3-cis-propenylpyrazine; 2-isopropenyl-3,6-dimethylpyrazine; 2-(2-methylpropyl)-3,5-dimethylpyrazine; 2,6-dimethyl-3-isobutylpyrazine; 2-(2-methylpropyl)-3,5,6-trimethylpyrazine, 2,3-dimethylpyrazine; trimethylpyrazine; 2,5-dimethyl-3-ethylpyrazine; tetramethylpyrazine; 2,3-diethyl-5-methylpyrazine; 2,5-dimethyl-3-propenylpyrazine; 2,3,5-trimethyl-6-isopropylpyrazine; 2-acetyl-4,5-dimethylpyrazine; 3,5-dimethyl-2-methylpropylpyrazine; 2,6-diethylpyrazine; 2,5-diethylpyrazine; 2-ethyl-3,5,6-trimethylpyrazine; 3,5-dimethyl-2-(n-propyl)pyrazine; 3,6-dimethyl-2-(n-propyl)pyrazine; 2,5-diethyl-3-methylpyrazine; 2,3-diethyl-5,6-dimethylpryazine; trans-3-methyl-2-(n-propyl)-6-(butenyl)pyrazine; 2,5,7-trimethyl-6,7-dihydro-5H-cyclopentapyrazine; and 2,5-dimethyl-3-ethylpyrazine; and combinations thereof.

* * * * *

UNITED STATES PATENT AND TRADEMARK OFFICE
CERTIFICATE OF CORRECTION

| | | |
|---|---|---|
| PATENT NO. | : 11,091,446 B2 | |
| APPLICATION NO. | : 15/468665 | |
| DATED | : August 17, 2021 | |
| INVENTOR(S) | : Michael Francis Dube et al. | |

It is certified that error appears in the above-identified patent and that said Letters Patent is hereby corrected as shown below:

On the Title Page

Column 2, under "Other Publications", Line 7, delete "Tobaco" and insert -- Tobacco --

On page 3, Column 1, under "U.S. Patent Documents", Line 45, after "Jr." insert -- et al. --

On page 4, Column 1, under "Other Publications", Line 56, delete "Kineticsof" and insert -- Kinetics of --

On page 4, Column 2, under "Other Publications", Line 12, delete "Carron" and insert -- Carvone --

On page 4, Column 2, under "Other Publications", Line 26, delete "[retrievedOct." and insert -- [retrieved Oct. --

On page 4, Column 2, under "Other Publications", Line 45, delete "No. I," and insert -- No. 1, --

On page 4, Column 2, under "Other Publications", Line 46, delete "Perflavoiy" and insert -- Perflavory --

On page 4, Column 2, under "Other Publications", Line 54, delete "Proeccedings" and insert -- Proceedings --

On page 5, Column 1, under "Other Publications", Line 5, delete "ration" and insert -- ratio --

In the Claims

At Column 34, Lines 57-58, in Claim 3, delete "dimethylypyrazine;" and insert -- dimethylpyrazine; --

At Column 35, Line 5, in Claim 7, delete "pyrazin; 2,5-3-" and insert -- pyrazine; 2,5-diethyl-3- --

Signed and Sealed this
Second Day of May, 2023

Katherine Kelly Vidal
*Director of the United States Patent and Trademark Office*

CERTIFICATE OF CORRECTION (continued)
U.S. Pat. No. 11,091,446 B2

At Column 35, Line 7, in Claim 7, delete "dimethylpryazine;" and insert -- dimethylpyrazine; --

At Column 35, Line 31, in Claim 13, delete "trisub stituted." and insert -- trisubstituted. --

At Column 36, Lines 10-11, in Claim 22, delete "2,5dimethyl-3-ethylpyrazine" and insert -- 2,5-dimethyl-3-ethylpyrazine --

At Column 36, Line 11, in Claim 22, delete "dimethylypyrazine;" and insert -- dimethylpyrazine; --

At Column 36, Line 62 (approx.), in Claim 25, delete "dimethylpryazine;" and insert -- dimethylpyrazine; --